(12) United States Patent
Kudaravalli et al.

(10) Patent No.: US 8,460,867 B2
(45) Date of Patent: Jun. 11, 2013

(54) METHODS OF TREATING PSYCHOSIS AND SCHIZOPHRENIA BASED ON POLYMORPHISMS IN THE CNTF GENE

(75) Inventors: Sridhar Kudaravalli, Chicago, IL (US); Mihael Hristos Polymeropoulos, Potomac, MD (US)

(73) Assignee: Novartis AG, Basel (CH)

( * ) Notice: Subject to any disclaimer, the term of this patent is extended or adjusted under 35 U.S.C. 154(b) by 267 days.

(21) Appl. No.: 12/477,469

(22) Filed: Jun. 3, 2009

(65) Prior Publication Data

US 2009/0239908 A1 Sep. 24, 2009

Related U.S. Application Data

(63) Continuation of application No. 11/754,470, filed on May 29, 2007, now abandoned, which is a continuation of application No. 10/497,503, filed as application No. PCT/EP02/13937 on Dec. 9, 2002, now abandoned.

(60) Provisional application No. 60/339,835, filed on Dec. 10, 2001.

(51) Int. Cl.
  *C07H 21/04* (2006.01)
  *C12Q 1/68* (2006.01)

(52) U.S. Cl.
  USPC ......... 435/6.1; 435/6.11; 435/6.12; 435/91.1; 435/91.2; 536/23.1; 536/24.3

(58) Field of Classification Search
  None
  See application file for complete search history.

(56) References Cited

U.S. PATENT DOCUMENTS

| | | |
|---|---|---|
| 3,539,573 A | 11/1970 | Schmutz et al. |
| 4,376,110 A | 3/1983 | David et al. |
| 4,683,202 A | 7/1987 | Mullis |
| 4,710,500 A | 12/1987 | Perregaard |
| 4,804,663 A | 2/1989 | Kennis et al. |
| 4,831,031 A | 5/1989 | Lowe et al. |
| 4,843,155 A | 6/1989 | Chomczynski |
| 4,879,288 A | 11/1989 | Warawa et al. |
| 4,946,778 A | 8/1990 | Ladner et al. |
| 4,965,188 A | 10/1990 | Mullis et al. |
| 5,112,838 A | 5/1992 | Perregaard et al. |
| 5,130,238 A | 7/1992 | Malek et al. |
| 5,169,766 A | 12/1992 | Schuster et al. |
| 5,229,382 A | 7/1993 | Chakrabarti et al. |
| 5,238,945 A | 8/1993 | Perregaard et al. |
| 5,302,509 A | 4/1994 | Cheeseman |
| 5,312,925 A | 5/1994 | Allen et al. |
| 5,510,270 A | 4/1996 | Fodor et al. |
| 5,539,083 A | 7/1996 | Cook et al. |
| 5,541,087 A | 7/1996 | Lo et al. |
| 5,556,752 A | 9/1996 | Lockhart et al. |
| 5,578,832 A | 11/1996 | Trulson et al. |
| 5,605,798 A | 2/1997 | Koster |
| 5,610,053 A | 3/1997 | Chung et al. |
| 5,625,126 A | 4/1997 | Lonberg et al. |
| 5,661,016 A | 8/1997 | Lonberg et al. |
| 5,679,524 A | 10/1997 | Nikiforov et al. |
| 5,726,044 A | 3/1998 | Lo et al. |
| 5,770,429 A | 6/1998 | Lonberg et al. |
| 5,789,650 A | 8/1998 | Lonberg et al. |
| 5,846,717 A | 12/1998 | Brow et al. |
| 5,854,033 A | 12/1998 | Lizardi |
| 5,866,404 A | 2/1999 | Bradshaw et al. |
| 5,945,283 A | 8/1999 | Kwok et al. |
| 6,001,567 A | 12/1999 | Brow et al. |
| 6,045,994 A | 4/2000 | Zabeau et al. |
| 2003/0092019 A1 | 5/2003 | Meyer et al. |
| 2004/0171056 A1 | 9/2004 | Stanton, Jr. |
| 2005/0059006 A1 | 3/2005 | Kudaravalli et al. |

FOREIGN PATENT DOCUMENTS

| | | |
|---|---|---|
| JP | 5-199879 | 8/1993 |
| JP | 2000346828 A | 12/2000 |
| JP | 2001131057 A | 5/2001 |
| JP | 2001243327 A | 9/2001 |
| WO | WO 9517676 | 6/1985 |
| WO | WO 8906700 | 7/1989 |
| WO | WO 8910414 | 11/1989 |
| WO | WO 9001069 | 2/1990 |
| WO | WO 9009455 | 8/1990 |
| WO | 0448707 | 10/1991 |
| WO | WO 9215712 | 9/1992 |
| WO | WO 9322456 | 11/1993 |
| WO | 329822 | 6/1994 |
| WO | WO 9511995 | 5/1995 |
| WO | WO 9820019 | 5/1998 |
| WO | WO 9820020 | 5/1998 |
| WO | WO 0101218 | 1/2001 |
| WO | 0115735 A1 | 3/2001 |
| WO | WO 03054226 | 7/2003 |

OTHER PUBLICATIONS

Lavendan et al. Pharmacogenomics, vol. 9, No. 3, pp. 289-301, 2008.*
Hirschhorn et al. (Genetics in Medicine. vol. 4, No. 2, pp. 45-61, Mar. 2002).*

(Continued)

*Primary Examiner* — Jeanine A Goldberg
(74) *Attorney, Agent, or Firm* — Stephen F. Swinton, Jr.; Hoffman Warnick LLC

(57) ABSTRACT

This invention relates to the use of the association between the 103 G>A polymorphism in the CNTF gene to determine antipsychotic treatment strategies in patients with psychotic disorders.

5 Claims, 1 Drawing Sheet

OTHER PUBLICATIONS

Ioannidis (Nature Genetics, vol. 29, pp. 306-309, Nov. 2001).*
Thome et al. (Neuroscience Letters, vol. 203, pp. 109-110, 1996).*
Tanaka et al., "Schizophrenic psychoses and the CNTF null mutation", Neuro., vol. 9, pp. 981-983.
Thome, et al., "Association between a null mutation in the human ciliary neurotrophic factor gene and increased . . . " Neuro. Letters, vol. 203, pp. 109-110, 1996.
Kelleher et al., "Advances in atypical antipsychotics for the treatment of schizophrenia . . . ", CNS Drugs, vol. 16, pp. 249-261, 2000.
Nothen et al., "CNTF and psychiatric disorders", Nature Gen., vol. 13, pp. 142-143, 1996.
Thome et al., "Ciliary neurotrophic factor null mutation and schizophrenia in a Swedish population", Psych. Gen., vol. 7, pp. 79-82, 1997.
Sakai, et al., "Schizophrenia and the ciliary neurotrophic factor gene: no evidence for association", Psych. Res., vol. 71, pp. 7-10, 1997.
Gelernter et al., "Ciliary neurotrophic factor null allele frequencies in schizophrenia . . . ", Amer. J. of Med. Gen., vol. 74, pp. 497-500, 1997.
Li et al, "CNTF and psychiatric disorders", Nature Gen., vol. 13, pp. 143-144, 1996.
Lam et al., "Sequence and structural organization of the human gene encoding ciliary neurotrophic factor", Gene, vol. 102, pp. 271-276, 1991.
Barany, "Genetic disease detection and DNA amplification using cloned thermostable ligase", PNAS, vol. 88, pp. 189-193 (1991).
Beasley, et al., "Olanzapine versus placebo and haloperidol", Neuropsychopharm., vol. 14, pp. 111-123 (1996).
Blanchard, et al., High-density oligonucleotide arrays, Biosensors & Bioelect., vol. 11, pp. 687-690 (1996).
Bradbury, et al., "Antibody Engineering: The cloning of hybridoma V regions for their ectopic expression in intracellular and intercellular immunization", Chap. 10, National Library of Medicine.
Burke, et al., "Microinjection of mRNA coding for an anti-golgi antibody inhibits intracellular transport of a viral membrane protein", Cell, vol. 36, pp. 847-856 (1984).
Cole, et al., "The EBV-hybridoma technique and its application to human lung cancer", Monoclonal Antibodies and Cancer Therapy, pp. 77-96 (1985).
Cote, et al., "Generation of human monoclonal antibodies reactive with cellular antigens", PNAS, vol. 80, pp. 2026-2030 (1983).
Egholm, et al., "PNA hybridizes to complementary oligonucleotides obeying the Watson-Crick hydrogen-bondign rules", Nature, vol. 365, p. 566-68 (1993).
Fodor, et al., "Light-directed, spatially addressable parallel chemical synthesis", Res. Article, pp. 767-773 (1991).
Froehler, et al., "Synthesis of DNA via deoxynucleoside H-phosphonate intermediates", IRL Press, pp. 5399-5407 (1986).
Goffeau, et al., "Life with 6000 genes", Science, vol. 274, pp. 546-567 (1996).
Gross, "How Charles Nicolle of the Pasteur institute discovered that epidemic typhus is transmitted by lice: reminiscences from my years at the Pasteur Institute in Paris", PNAS, vol. 93, pp. 10539-10640 (1996).
Guatelli, et al., "Isothermal, in vitro amplification of nucleic acids by a multienzyme reaction modeled after retroviral replication", PNAS, vol. 87, pp. 1874-1878 (1990).
Kohler, et al., "Continuous cultures of fused cells secreting antibody of predefined specificity", Nature, vol. 256, pp. 495-497 (1975).
Judson, "Genetic algorithms and their use in chemistry", Rev. in Comp. Chem., vol. 10, pp. 1-66 (1997).
Kay, et al., "Transgenic mouse for heterologous antibody production—containing DNA encoding human Immunoglobulin components", Abstract No. 011319506 (1997).
Kay, et al., "The positive and negative syndrome scale for schizophrenia", Schizo. Bull., vol. 13, pp. 261-276 (1987).
Kozbor, et al., "The production of monoclonal antibodies from human lymphocytes", Immun. Today, vol. 4, pp. 72-79 (1983).
Krug, et al., "First-strand cDNA synthesis primed with Oligo(dT)", Meth. in Enzymol., vol. 152, pp. 316-325 (1987).
Kuimelis, et al., "Structural analogues of TaqMan probes for real-time quantitative PCR", Nuc. Acids Symp. Series, No. 37, pp. 255-256 (1997).
Kwoh, et al, "Transcription-based amplification system and detection of amplified human immunodeficiency virus type 1 with a bead-based sandwich hybridization format", PNAS, vol. 86, pp. 1173-1177 (1989).
Lizardl, et al., "Exponential amplification of recombinant-RHA hybridization probes", Biotech., vol. 6, pp. 1197-1202 (1988).
Lockhart, et al., "Expression monitoring by hybridization to high-density oligonucleotide arrays", Nature Biotech., vol. 14, pp. 1675-1680 (1996).
Maskos, et al., "Oligonucleotide hybridizations on glass supports: a novel linker for oligonucleotide synthesis and hybridization properties of oligonucleotides synthesised in situ", Nuc. Acids Res., vol. 20, pp. 1679-1684 (1992).
McBride, et al., An investigation of several deoxynucleoside phosphoramidites useful for synthesizing deoxyoligounucleotides, Tetrahedron Letters, vol. 24, pp. 245-248(1983).
Michalatos-Beloin, et al., "Molecular haplotyping of genetic markers 10 kb apart by allele-specific long-range PCR", Nuc. Acids Res., vol. 24, pp. 4841-4843 (1996).
Modrich, "Mechanisms and biological effects of mismatch repair", Ann. Rev. Gen., vol. 25, pp. 229-253 (1991).
Morrison, et al, "Chimeric human antibody molecules: mouse antigen-binding domains with human constant region domains", PNAS, vol. 81, pp. 6851-6855 (1984).
Mullah, et al., "Efficient synthesis of double dye-labeled oligodeoxyribonucleotide probes and their application in a real time PCR assay", Nuc. Acids Res., vol. 26, pp. 1026-1031 (1998).
Morgan et al., "Analysis of intracellular protein function by antibody injection", Immun. Today, vol. 9, pp. 84-88 (1988).
Neuberger, et al., "Recombinant antibodies possessing novel effector functions" Nature, vol. 312, pp. 604-608 (1984).
Nguyen, et al., "Differential gene expression in the murine thymus assayed by quantitative hybridization of arrayed cDNA clones", Genomics, vol. 29, pp. 207-216 (1995).
Pietu, et al., "Novel gene transcripts preferentially expressed in human muscles revealed by quantitative hybridization of a high density cDNA array", Genome Res., pp. 492-503 (1996).
Ruano, et al., "Genotyping and haplotyping of polymorphisms directly from genomic DNA via coupled amplification and sequencing (CAS)", Nuc. Acids Res., vol. 19, pp. 6877-6882 (1991).
Ruano, et al., "Direct haplotyping of chromosomal segments from multiple heterozygotes via allele-specific PCR amplification", Nuc. Acids Res., vol. 17, pp. 8392 (1989).
Ryan, et al., "Non PCR-dependent detection of the factor V Leiden mutation from genomic DNA using a homogenous invader microtiter plate assay", Mol. Diagn., vol. 4, pp. 135-144 (1999).
Schena, et al, "Quantitative monitoring of gene expression patterns with a complementary DNA microarray", Science, vol. 270, pp. 467-470 (1995).
Seifter, et al., "Analysis for protein modifications and nonprotein cofactors", Meth. in Enzym., vol. 182, pp. 626-647 (1990).
Shalon, et al., "A DNA microarray system for analyzing complex DNA samples using two-color fluorescent probe hybridization", Genome Res., pp. 639-645 (1996).
Sheffield, et al., "Attachment of a 40-base-pair G+C-rich sequence (GC-clamp) to genomic DNA fragments by the polymerase chain reaction results in improved detection of single-base changes", PNAS, vol. 86, pp. 232-236 (1989).
Shi, "Enabling large-scale pharmacogenetic studies by high-throughput mutation detection and genotyping technologies", Clin. Chem., vol. 47, pp. 164-172 (2001).
Stephens, "Single-nucleotide polymorphisms, haplotypes, and their relevance to pharmacogenetics", Mol. Diag., vol. 4, pp. 309-317 (1999).
Takeda, et al., "Construction of chimaeric processed immunoglobulin genes containing mouse variable and human constant region sequences", Nature, vol. 314, pp. 452-454 (1985).
Turki, et al., "Genetic polymorphisms of the B2-adrenergic receptor in nocturnal and nonnocturnal asthma", J. Clin. Invest., vol. 95, pp. 1635-1641 (1995).

Walker, et al., "Isothermal in vitro amplification of DNA by a restriction enzyme/DNA polymerase system", PNAS, vol. 89, pp. 392-396 (1992).

Wartell, et al., "Detecting base pair substitutions in DNA fragments by temperature-gradient gel electrophoresis", Nuc. Acids Res., vol. 18, pp. 2699-2705 (1990).

Winter, et al., "A method to detect and characterize point mutations in transcribed genes: amplification and overexpression of the mutant c-Ki-ras allele in human tumor cells", PNAS; vol. 82, pp. 7575-7579 (1985).

Prince, J.T., "Preliminary Amendment," filed with USPTO for U.S. Appl. No. 10/497,503 on Jun. 3, 2004, pp. 1-9.

Goldberg, J.A., "Restriction Requirement," issued by USPTO for U.S. Appl. No. 10/497,503 on Jul. 19, 2006, pp. 1-6.

Prince, J.T., "Response to Restriction Requirement," filed with USPTO for U.S. Appl. No. 10/497,503 on Sep. 15, 2006, p. 1.

Goldberg, J.A., "Non-Final Office Action," issued by USPTO for U.S. Appl. No. 10/497,503 on Nov. 30, 2006, pp. 1-14.

Prince, J.T., "Amendment," filed with USPTO for U.S. Appl. 10/497,503 on May 25, 2007, pp. 1-15.

Goldberg, J.A., "Final Office Action," issued by USPTO for U.S. Appl. No. 10/497,503 on Aug. 10, 2007, pp. 1-15.

Swinton, Jr., S.F., "After-Final Amendment," filed with USPTO for U.S. Appl. No. 10/497,503 on Feb. 7, 2008, pp. 1-13.

Goldberg, J.A., "Office Action," issued by USPTO for U.S. Appl. No. 10/497,503 on Apr. 15, 2008, pp. 1-14.

Swinton, Jr., S.F., "Amendment," filed with USPTO for U.S. Appl. No. 10/497,503 on Jul. 14, 2008, pp. 1-14.

Goldberg, J.A., "Final Office Action," issued by USPTO for U.S. Appl. No. 10/497,503 on Nov. 5, 2008, pp. 1-12.

China Patent Office, "First Office Action," issued Apr. 3, 2006, with translation, pp. 1-5.

Zhongzi Law Office, "Office Action Response," filed Sep. 3, 2006, with translation, pp. 1-14.

China Patent Office, "Second Office Action," issued Jan. 23, 2009, pp. 1-6.

Zhongzi Law Office, "Second Office Action Response," filed May 2009, pp. 1-6.

Japan Patent Office, "First Official Action," issued Jan. 27, 2009, pp. 1-8.

Aoyama & Partners Law Firm, "Response to First Official Action," filed May 20, 2009, pp. 1-5.

European Patent Office, "Examination Report—Communication pursuant to Article 96(2) EPC," issued Apr. 3, 2007, pp. 1-6.

Hofstetter, A., "Response to Communication pursuant to Article 96(2) EPC," Oct. 11, 2007, pp. 1-8.

PCT, "International Search Report," Publication No. WO 2003/054226 A3, Jul. 3, 2003, pp. 1-8.

PCT, "International Preliminary Examination Report," Mar. 10, 2004, pp. 1-2.

Thome et al., "A null mutation allele in the CNTF gene and schizophrenic psychoses," NeuroReport: Genetics of Nervous System Disease, 1996, pp. 1413-1416, vol. 7, Abstract Only.

Corbett et al., "Iloperidone: Preclinical Profile and Early clinical Evaluation," 1997, pp. 120-147, CNS Drug Reviews, vol. 3, No. 2, 1997 Neva Press, Branford, CT.

Hu et al., "Psychoactive Drugs Being Developed in the USA in 1998," Dec. 1999, pp. 208-209, Chinese Journal of New Drugs, vol. 8, No. 3, Abstract.

Takahashi et al., "A null mutation in the human CNTF gene is not causally related to neurological diseases," May 1994, pp. 79-84, Nature Genetics, vol. 7.

Jain, "An assessment of iloperidone for the treatment of schizophrenia," 2000, pp. 2935-2943, Expert Opinion on Investigational Drugs, vol. 9, No. 12.

\* cited by examiner

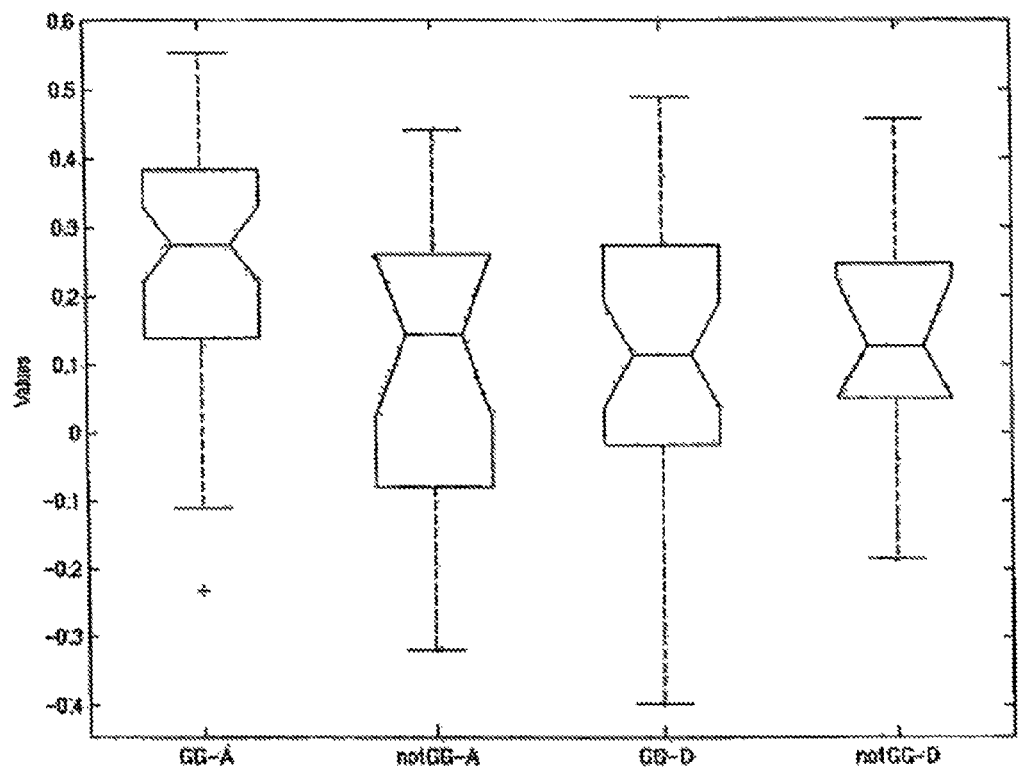
Average Percent Change in GG TOTPANSS and Not-GG TOTPANSS
GG-A: Iloperidone Dose A (12-16 mg), GG individuals only
notGG-A: Iloperidone Dose A (12-16 mg), individuals without GG genotype
GG-D: Placebo, GG individuals only
notGG-D: Placebo, individuals without GG genotype
+ - outlier

METHODS OF TREATING PSYCHOSIS AND SCHIZOPHRENIA BASED ON POLYMORPHISMS IN THE CNTF GENE

CROSS-REFERENCE TO RELATED APPLICATIONS

This application is a continuation of U.S. patent application Ser. No. 11/754,470, filed 29 May 2007 now abandoned, which is a continuation of U.S. patent application Ser. No. 10/497,503, filed 29 Jun. 2004 now abandoned, which is a U.S. National stage application of PCT/EP02/13937, filed 9 Dec. 2002, which claims priority to U.S. Provisional Patent Application No. 60/339,835, filed 10 Dec. 2001, each of which is hereby incorporated herein.

BACKGROUND OF THE INVENTION

1. Field of the Invention

The present invention belongs to the fields of pharmacology, medicine and medicinal chemistry and provides methods to treat psychotic conditions including schizophrenia and related conditions. In particular, this invention relates to the use of genomic analysis to determine a patient's responsiveness to antipsychotic medication including Iloperidone and methods to determine optimal treatment strategies.

2. Description of the Related Art

Ciliary Neurotrophic Factor (CNTF) was originally known as a survival factor for chick ciliary neurons in vitro but has more recently shown to be a survival factor for different neuronal cell types. CNTF is involved with the prevention of degeneration of motor axons and is a member of the interleukin-6 cytokine family. Barbin et al. used a survival assay for neurons from chick embryonic ciliary ganglia to report the neurotrophic activity of CNTF from chick eye. See, Barbin, G et al., *J. Neurochem.* 43:1468-1478, 1984. CNTF was also shown to have actions on sympathetic and sensory neurons in this study.

The CNTF gene also holds hope for the treatment of amyotrophic lateral sclerosis (ALS) and other similarly related disorders. In homozygous pmn/pmn mice a disorder occurs in which the hind limbs have a progressive motor neuropathy which becomes evident at the end of the third postnatal week. All the mice die six to seven weeks after birth from respiratory paralysis. Sendtner et al. treated the mice with CNTF and successfully improved motor function and reduced the morphologic symptoms of neural degeneration even when degenerative alterations were already present. See, Sendtner et al., *Nature* 358: 502-504, 1992.

Greater understanding was gained when CNTF gene expression was eliminated in mice by homologous recombination and the progressive atrophy and loss of motor neurons still took place, accompanied by a small reduction in muscle strength, see, Masu et al. *Nature* 365: 27-32, 1993. The authors of this study, stated that these results demonstrate that expression of the gene is not essential for the development of spinal motor neurons as determined by morphologic criteria, but that it is essential for maintenance of function in motor neurons in the postnatal period.

Takahashi et al. had similar findings in the lack of effects in the CNTF knockout mice. They found that roughly 2.5% of the Japanese population are homozygous for mutations that inactivate the CNTF gene, see, Takahashi et al. *Nature Genet.* 7: 79-84, 1994. Those that lack CNTF seem not to be adversely affected and have not shown any related neurologic defects.

CNTF receptor subunits share similar sequences with the leptin (LEP) receptor. Studies suggest that both CNTF and LEP cytokines have the ability to signal the hypothalamic satiety centers. These results came after systemic administration of CNTF and LEP to ob/ob mice, which led to rapid induction of the tis-11 primary response gene in the arcuate nucleus. When ob/ob mice, lacking a functional leptin, were treated with CNTF the adiposity, hyperphagia, and hyperinsulinemia associated with leptin deficiency were reduced. In contrast to leptin, CNTF also reduced obesity-related phenotypes in db/db mice, which lack a functional leptin receptor, and in mice with diet-induced obesity, which are partially resistant to the actions of leptin.

CNTF protein is stored inside adult glial cells, perhaps awaiting release by some mechanism provoked by injury. It may not be essential for development and may, in fact, act in response to injury or some other type of stress. CNTF was characterized as a trophic factor for motor neurons in the ciliary ganglion and spinal cord.

Polymorphism in the CNTF Gene

A polymorphism in the CNTF gene has been identified. The CNTF gene is located on 11q12.2 and the polymorphism is 103 G>A in GenBank sequence X55890 (Version 1) (see PubMed: 9285965). A mutation in an acceptor splice site caused the mRNA to splice incorrectly, thereby abolishing expression of the CNTF protein. The nucleotide change was a G to A transition at position −6 of the receptor splice site, leading to a frameshift from amino acid 39, resulting in a stop codon 24 amino acids downstream. The irregular mRNA was expected to code for a truncated protein 62 amino acids long (FS63 TER).

Analysis of tissue samples and transfection of CNTF minigenes into cultured cells demonstrated, that the mutated allele expressed only the mutated mRNA species. The homozygous mutant gene is not translated into protein as is shown by the finding that antibodies that recognise both the normal and mutated CNTF show complete lack of CNTF immunoreactivity in peripheral nerve tissue from a homozygous mutant subject. See, Takahashi et al. *Nature Genet.* 7: 79-84, 1994.

Psychotic Disorders

Psychoses exact a tremendous emotional and economic toll on the patients, their families, and society as a whole. Psychotic conditions, such as schizophrenia and related disorders (e.g. schizoaffective disorder), and including affective disorders (mood disorders) with psychotic symptoms (e.g. Bipolar Disorder) are complex and heterogeneous diseases of uncertain aetiology that afflict a large percentage of all populations world-wide.

Schizophrenia is characterised as having both "positive symptoms" (hallucinations, delusions, and conceptual disorganisation) and "negative symptoms" (apathy, social withdrawal, affect, and poverty of speech). Abnormal activity of the neurotransmitter dopamine is a hallmark of schizophrenia. Dopaminergic activity is reduced in the mesocortical system (resulting in negative symptoms) and is enhanced in the mesolimbic system (resulting in positive or psychotic symptoms). Several other neurotransmitters are involved, including serotonin, glutamate, and gamma-aminobutyric acid (GABA).

Antipsychotic drugs, in one form or another, have long been the basis of treatment of psychotic disorders. These drugs are sometimes used in combination with a mood regulating medication such as lithium or an antidepressant. For many years, schizophrenia was treated with classical antipsychotic drugs, the neuroleptics, that block central dopamine receptors. The neuroleptics are effective for treating the positive symptoms of schizophrenia, but have little or no effect on the negative symptoms. The ability of these drugs to antagonize dopamine receptors correlates with antipsychotic efficacy. Neuroleptic drugs include phenothiazines including aliphatics (e.g., chlorpromazine), piperidines (e.g., thioridazine), and piperazines (e.g., fluphenazine); butyrophenones (e.g., haloperidol); thioxanthenes (e.g., flupenthixol); oxoindoles (e.g., molindone); dibenzoxazepines (e.g., loxapine) and diphenylpiperidines (e.g., pimozide). Unfortunately, neuroleptics-resistant negative symptoms account for most of the social and vocational disability caused by schizophrenia. Further, neuroleptics cause extrapyramidal symptoms, including rigidity, tremor, bradykinesia (slow movement), and bradyphrenia (slow thought), as well as tardive dyskinesias and dystonias. For treatment of psychosis with medications, see, Textbook of Psychopharmacology, Schatzberg A F and Nemeroff C B, Editors, American Psychiatric Press. Wash. D.C. 1995.

Progress in the treatment of psychotic conditions has been achieved through the introduction of new, atypical antipsychotic agents. The side effect profile of these atypical antipsychotics is far superior to that of traditional agents. The atypical antipsychotics are a different class of antipsychotic drugs which have a different receptor binding profile and effectiveness against the symptoms of schizophrenia. The essential feature of an atypical antipsychotic is less acute extrapyramidal symptoms, especially dystonias, associated with therapy as compared to a typical antipsychotic such as haloperidol. Clozapine, the prototypical atypical antipsychotic, differs from the typical antipsychotics with the following characteristics: (1) greater efficacy in the treatment of overall psychopathology in patients with schizophrenia non-responsive to typical antipsychotics; (2) greater efficacy in the treatment of negative symptoms of schizophrenia; and (3) less frequent and quantitatively smaller increases in serum prolactin concentrations associated with therapy (Beasley, et al., Neuropsychopharmacology, 14(2), 111-123, (1996)).

Atypical antipsychotics bind central serotonin2 (5-HT2) receptors in addition to D2 dopamine receptors. Unlike the neuroleptics, they improve negative as well as positive symptoms. They cause minimal extrapyramidal symptoms and rarely cause tardive dyskinesias, akathisia, or acute dystonic reactions. The first atypical antipsychotic drug approved for the treatment of schizophrenia was clozapine. Clozapine is effective for the treatment of schizophrenia, especially for subjects who do not respond to traditional neuroleptic therapy.

The treatment of psychotic disorders with antipsychotic agents has steadily improved over the years. However, up to now there has been no means, other than trial and error, to determine which patients will respond to an antipsychotic agent and what dose level a given patient may require to produce a therapeutic response without severe side effects. Since all antipsychotic agents, even the newer atypical ones, have significant side effects including extrapyramidal symptoms, such as rigidity, tremor, bradykinesia (slow movement), and bradyphrenia (slow thought), as well as tardive dyskinesias and dystonias this "trial and error" period could be time consuming, unpleasant and even dangerous for the patient and increased the likelihood of non-compliance. These side effects and toxic effects are dose dependent. Therefore there is a great need to develop means to determine whether or not a patient will respond to an antipsychotic agent and what dose range will be effective in a particular patient while minimising side effects.

SUMMARY OF THE INVENTION

The present invention answers this need by providing methods for treating a patient suffering from or susceptible to a psychotic disorder, including but not limited to schizophrenia and mood disorders with psychotic symptoms, comprising determining for the two copies of the CNTF gene present in the individual, the identity of the nucleotide pair at the polymorphic site 103 G>A, (the CNTF gene is located on 11q12.2 the polymorphism is 103 G>A in GenBank sequence X55890 (Version 1)). This nucleotide variation results in the creation of a new splice acceptor site, an altered mRNA and a resultant aberrant protein (FS63 TER), see, Pub Med ID No. 9285965. The determination of treatment is based on the knowledge that if both nucleotide pairs are G or if both nucleotide pairs are A then the individual will be responsive to treatment with antipsychotic medications including but not limited to Iloperidone. If one nucleotide pair is A and one is G it can be expected that the individual will be less responsive to antipsychotic medications, including but not limited to Iloperidone and may require a higher dose or an adjunctive therapy in addition to, or instead of an antipsychotic. On the basis of this information the individual can be administered an effective amount of an appropriate antipsychotic medication designed to minimise side effects and to maximise response and patient compliance.

Therefore, in one aspect, this invention provides a method of treating a psychotic disorder in a patient in need of such treatment comprising, determining for the two copies of the CNTF gene present in the individual the identity of the nucleotide pair at the polymorphic site 103 G>A in GenBank sequence reference No. X55890 (Version 1) wherein, if both nucleotide pairs are G or if both are A then the individual is treated with Iloperidone and wherein, if one nucleotide pairs is A and one is G then the individual is treated with alternative therapy or with Iloperidone in combination with an alternative therapy.

In another aspect, this invention provides a method to treat a psychotic disorder in a patient in need of such treatment comprising, assaying for the presence of CNTF protein in the said patients body fluids or tissues, wherein, if CNTF protein is found in normal levels or is undetectable, indicating GG or AA genotype respectively, the patient is treated with Iloperidone, and if the CNTF protein is found in intermediate levels the patient is treated with alternative therapy or with Iloperidone in combination with an alternative therapy.

In a further aspect, this invention provides a method to treat a psychotic disorder in a patient in need of such treatment comprising, detecting a level of mRNA expression corresponding to the G variant of the CNTF gene at the polymorphic site 103 G>A in GenBank sequence reference No. X55890 (Version 1), detecting a level of mRNA expression corresponding to the A variant of the CNTF gene at the polymorphic site 103 G>A in GenBank sequence reference No. X55890 (Version 1), comparing the levels of mRNA detected in (a) and (b) above wherein, if (a) is two times or more the value of (b), or if (b) is two times or more the value of (a), the patient is treated with Iloperidone (anti-psychotic medication), and if (a) and (b) are of similar value, the patient is treated with alternative therapy or with Iloperidone in combination with an alternative therapy.

In another embodiment, this invention provides a method to choose subjects for inclusion in a clinical study of an anti-psychotic medication comprising, determining for the two copies of the CNTF gene present in the individual, the identity of the nucleotide pair at the polymorphic site 103 G>A in GenBank sequence reference No. X55890 (Version 1) wherein, the individual is included in the study if both nucleotide pairs are G or both nucleotide pairs are A, and the individual is excluded from the study if one nucleotide pair is A and one is G.

Another aspect of the invention, is a kit for use in determining treatment strategy for a patient with a psychotic disorder comprising, an antibody able to recognize and bind to the polypeptide expression product of the CNTF gene, a container suitable for containing the said antibody and a sample of body fluid from the said individual wherein the antibody can contact the CNTF polypeptide if it is present, and means to detect the combination of the said antibody with CNTF polypeptide and also including instructions for use of the kit.

A further aspect of the invention, is a kit for use in determining treatment strategy for a patient with a psychotic disorder comprising, a polynucleotide able to recognize and bind to the mRNA expression product of the CNTF gene, a container suitable for containing the said polynucleotide and a sample of body fluid from the said individual wherein the said polynucleotide can contact the CNTF mRNA, if it is present, and means to detect the combination of the said polynucleotide with the CNTF mRNA and also including instructions for use of kit.

In another aspect, this invention provides a kit for use in determining a treatment strategy for a patient with a psychotic disorder comprising, a polynucleotide able to recognize and bind to some portion of the DNA sequence of the CNTF gene, a container suitable for containing the said polynucleotide and a sample of body fluid from the said individual wherein the polynucleotide can contact the CNTF DNA sequence if it is present, and means to detect the combination of the said polynucleotide with the CNTF DNA sequence and including instructions for use of kit.

In a further aspect, this invention provides a method for determining the responsiveness of an individual with a psychotic disorder to treatment with Iloperidone, comprising, determining, for the two copies of the CNTF gene present in the individual, the identity of a nucleotide pair at a polymorphic site in the region of the CNTF gene that is in linkage disequilibrium with the polymorphic site at CNTF 103 G>A in GenBank sequence reference No. X55890 (Version 1); and assigning the individual to a good responder group if the nucleotide pair at a polymorphic site in the region of the CNTF gene that is in linkage disequilibrium with the polymorphic site at 103 G>A, indicates that, at the CNTF polymorphic site at 103 G>A, both nucleotide pairs are GC or both pairs are AT and to a low responder group if said nucleotide pair indicates that one pair is AT and one pair is GC at the CNTF 103 G>A site.

In another aspect, this invention provides a kit for the identification of a patient's polymorphism pattern at the CNTF polymorphic site at 103 G>A, said kit comprising a means for determining a genetic polymorphism pattern at the CNTF polymorphic site at 103 G>A.

In another embodiment, the invention relates to a kit described in the preceding paragraph, which further comprises a DNA sample collecting means.

Another embodiment of the invention is a kit described in the preceding paragraphs, wherein the means for determining a genetic polymorphism pattern at the CNTF polymorphic site at 103 G>A comprise at least one CNTF genotyping oligonucleotide.

A further embodiment of the invention is a kit according to the preceding paragraphs, wherein the means for determining a genetic polymorphism pattern at the CNTF polymorphic site at 103 G>A comprise two CNTF genotyping oligonucleotides.

In another embodiment, the invention relates to a kit as described in the preceding paragraphs, wherein the means for determining a genetic polymorphism pattern at the CNTF polymorphic site at 103 G>A comprise at least one CNTF genotyping primer composition comprising at least one CNTF genotyping oligonucleotide.

A further embodiment of the invention is a kit as described in the preceding paragraphs, wherein the CNTF genotyping primer composition comprises at least two sets of allele specific primer pairs.

Another embodiment of the invention provides a kit according to the preceding paragraphs, wherein the two CNTF genotyping oligonucleotides are packaged in separate containers.

A further embodiment of the invention is a method, wherein a kit according to the aforementioned embodiments is used to determine for the two copies of the CNTF gene present in the individual the identity of the nucleotide pair at the polymorphic site 103 G>A in GenBank sequence reference No. X55890 (Version 1) and/or for determining, for the two copies of the CNTF gene present in the individual, the identity of a nucleotide pair at a polymorphic site in the region of the CNTF gene that is in linkage disequilibrium with the polymorphic site at CNTF 103 G>A in GenBank sequence reference No. X55890 (Version 1)

Another aspect of the invention is a kit for the identification of mRNA expression of the CNTF gene, said kit comprising a means for determining the mRNA product of the CNTF gene.

A further embodiment of the present invention is a kit described in the preceding paragraph, wherein the means for determining the mRNA product of the CNTF gene comprises a polynucleotide capable of binding to the mRNA expression product of the CNTF gene.

In another embodiment, this invention provides a kit for the identification of mRNA expression of the CNTF gene according to the preceding paragraphs, wherein the means for determining the mRNA product of the CNTF gene comprises at least one polynucleotide specific for one of the variants of the CNTF gene at the polymorphic site 103 G>A.

In a further embodiment, the invention provides a kit for the identification of mRNA expression of the CNTF gene, wherein the polynucleotide is specific for mRNA expression of the G variant of the CNTF gene at the polymorphic site 103 G>A.

Another embodiment of the invention is a kit for the identification of mRNA expression of the CNTF gene, wherein the polynucleotide is specific for mRNA expression of the A variant of the CNTF gene at the polymorphic site 103 G>A.

In another embodiment, this invention provides a kit according to the preceding paragraph, wherein the polynucleotide is specific for the irregular mRNA coding for a truncated protein of 62 amino acids.

In a further embodiment, the invention provides a kit for the identification of mRNA expression of the CNTF gene as described in the preceding claims, wherein the polynucleotide is binding the mRNA expression product of the G or A variant of the CNTF gene under stringent hybridization conditions.

Another embodiment of the invention is a kit for the identification of mRNA expression of the CNTF gene described in the preceding claims, wherein the means for determining the mRNA product of the CNTF gene comprise at least two polynucleotides, wherein one polynucleotide is specific for mRNA expression of the G variant of the CNTF gene at the polymorphic site 103 G>A, and the other polynucleotide is specific for mRNA expression of the A variant of the CNTF gene at the polymorphic site 103 G>A.

In a further embodiment of the invention, a kit described in the preceding paragraph is provided, wherein the two polynucleotides are packaged in separate containers.

Another embodiment of the invention is a method, wherein one of the aforementioned embodiments for the identification of mRNA expression of the CNTF gene of the invention is used for either (a) detecting a level of mRNA expression corresponding to the G variant of the CNTF gene at the polymorphic site 103 G>A in GenBank sequence reference No. X55890 (Version 1), and/or (b) detecting a level of mRNA expression corresponding to the A variant of the CNTF gene at the polymorphic site 103 G>A in GenBank sequence reference No. X55890 (Version 1).

In another aspect, this invention provides a kit for the identification of a patient's CNTF protein level comprising a means for detecting the polypeptide expression product of the CNTF gene.

A further embodiment of the invention is a kit described in the preceding paragraph, wherein the means comprises an antibody recognizing the CNTF polypeptide.

In another embodiment, the invention provides a kit according to the preceding paragraph, wherein the binding of the antibody is within a $K_D$ range of $10e^{-6}$ to $10e^{-13}$, preferable within a range of $10e^{-8}$ to $10e^{-12}$.

Another embodiment of the invention is a method, wherein one of the aforementioned kits for the identification of a patient's CNTF protein level is used for assaying for the presence of CNTF protein in the patients body fluids or tissues.

In another embodiment, this invention provides a kit according to the preceding claims, further comprising a means for collecting a body fluid or a tissue sample.

Further embodiments of the invention provide for a method of treating a psychotic disorder in a patient in need of such treatment, a method to choose subjects for inclusion in a clinical study of an antipsychotic medication, or a method for determining the responsiveness of an individual with a psychotic disorder to treatment with Iloperidone, wherein said method is performed ex vivo.

BRIEF DISCUSSION OF THE DRAWINGS

FIG. 1 shows the average percent change in GG TOTPANSS and not-GG TOTPANSS as discussed in Example 1.

DESCRIPTION OF THE PREFERRED EMBODIMENTS

Thus, in a first aspect, the invention provides methods of determining the responsiveness of an individual with a psychotic disorder to treatment with an antipsychotic medication including but not limited to Iloperidone. These methods comprise determining the genotype or haplotype of the CNTF gene and making the determination of responsiveness based on the presence or absence of one or more polymorphic variants in the CNTF gene. The CNTF gene is located on 11q12.2 and the polymorphism is 103 G>A in GenBank sequence X55890 (Version 1). This nucleotide variation results in the creation of a new splice acceptor site, an altered mRNA and a resultant aberrant protein, see, Pub Med ID No. 9285965.

The detection of these polymorphisms can be used to determine or predict the responsiveness of the individual to a particular antipsychotic agent. In addition, the polymorphisms can be detected directly or by detecting the characteristic mRNA of the polymorphic variant gene as opposed to the more common CNTF type.

Furthermore, detection of the polypeptide (protein) expression product of the CNTF gene in body fluids or tissues can be used to determine the presence or absence of the polymorphism and, the relative level of the polypeptide expression product can be used to determine if the polymorphism is present in a homozygous or heterozygous state and therefore the responsiveness of the patient to antipsychotic agents.

Therefore, one embodiment of the present invention is a method for the determination of the presence or absence of the polymorphism in a patient by identifying the presence of the protein expression product of the CNTF gene. Studies have shown that the mRNA from the A variant is not translated into a polypeptide expression product. Therefore, if normal amounts of the protein is found in the body fluids or tissue samples of the patient then the patient is presumed to have the more common homozygous G variant and will respond to antipsychotic agents. If the level of CNTF protein expression is undetectable then the patient is presumed to have the homozygous A polymorphism and would be expected to also be an antipsychotic medication responder. However, if the patient is found to have an intermediate level of the protein in body fluids or tissue samples then the patient will be expected to have heterozygous polymorphism with one allele containing G and one containing A at the polymorphic site. In this case the patient would be expected to be a non-responder to antipsychotic medication, including Iloperidone, and treatment with an antipsychotic such as Iloperidone alone would not be indicated.

As used herein, the term "normal level" when used in reference to the level of the polypeptide expression product of the CNTF gene measured in a body fluid or body tissue means that the measured level is within one standard deviation of the mean level of CNTF gene polypeptide expression product determined in at least 10 individuals known to have the G variant at both loci at the 103 G>A polymorphic site in the human CNTF gene (in the sequence with GenBank accession number X55890 (Version 1)) when determined in the same body fluid or tissue type and by the same assay technique.

As used herein the term "intermediate level" when used in reference to the level of the polypeptide expression product of the CNTF gene measured in a body fluid or body tissue means that the measured level is more than one standard deviation below the mean level of CNTF gene polypeptide expression product determined in at least 10 individuals known to have the G variant at both loci at the 103 G>A polymorphic site in the human CNTF gene (in the sequence with GenBank accession number X55890 (Version 1)) when determined in the same body fluid or tissue type and by the same assay technique.

In another embodiment, the present invention provides methods for determining a patients responsiveness to antipsychotic agents and to develop treatment strategies for a patient with a psychotic disorder. These methods comprise measuring the amount and ratio of mRNAs corresponding to the more common variant of the CNTF gene, i.e., G at site 103, versus the less common polymorphic variant with A in place of G. In this embodiment the ratio of the two mRNAs is determined in a sample of the patients body fluid or body tissue. If all the mRNA is from the G variant then the patient will be responsive to treatment with antipsychotic agents including Iloperidone. If all the mRNA is from the A variant then the patient will also be responsive to treatment with antipsychotic agents such as Iloperidone. However, if both types of mRNA are found then the patient is heterozygous for the polymorphism and will be expected to be poorly responsive to treatment with antipsychotic medication, including Iloperidone and alternative treatment strategies will be considered.

One of skill in the art will readily recognize that, in addition to the specific polymorphisms disclosed herein, any polymorphism that is in linkage disequilibrium with the said polymorphism can also serve as a surrogate marker indicating responsiveness to the same drug or therapy as does the single nucleotide polymorphism (SNP) that it is in linkage disequilibrium with. Therefore, any SNP in linkage disequilibrium with the SNPs disclosed in this specification, can be used and is intended to be included in the methods of this invention.

Identification and Characterization of SNPs

Many different techniques can be used to identify and characterize SNPs, including single-strand conformation polymorphism analysis, heteroduplex analysis by denaturing high-performance liquid chromatography (DHPLC), direct DNA sequencing and computational methods, see Shi M M, *Clin Chem* 2001, 47:164-172. Thanks to the wealth of sequence information in public databases, computational tools can be used to identify SNPs in silico by aligning independently submitted sequences for a given gene (either cDNA or genomic sequences). Comparison of SNPs obtained experimentally and by in silico methods showed that 55% of candidate SNPs found by SNPFinder(http://Ipgws.nci.nih.gov:82/perl/snp/snp_cgi.pl) have also been discovered experimentally, see, Cox et al. *Hum Mutal* 2001, 17:141-150. However, these in silico methods could only find 27% of true SNPs.

The most common SNP typing methods currently include hybridization, primer extension and cleavage methods. Each of these methods must be connected to an appropriate detection system. Detection technologies include fluorescent polarization, (see Chan X et al. *Genome Res* 1999, 9:492-499), luminometric detection of pyrophosphate release (pyrosequencing), (see Ahmadiian A et al. *Anal Biochem* 2000, 280:103-10), fluorescence resonance energy transfer (FRET)-based cleavage assays, DHPLC, and mass spectrometry, (see Shi M M, *Clin Chem* 2001, 47:164-172 and U.S. Pat. No. 6,300,076 B1). Other methods of detecting and characterizing SNPs are those disclosed in U.S. Pat. No. 6,297,018 B1 and 6,300,063 B1. The disclosures of the above references are incorporated herein by reference in their entirety.

In a particularly preferred embodiment the detection of the polymorphism can be accomplished by means of so called INVADER™ technology (available from Third Wave Technologies Inc. Madison, Wis.). In this assay, a specific upstream "invader" oligonucleotide and a partially overlapping downstream probe together form a specific structure when bound to complementary DNA template. This structure is recognized and cut at a specific site by the Cleavase enzyme, and this results in the release of the 5' flap of the probe oligonucleotide. This fragment then serves as the "invader" oligonucleotide with respect to synthetic secondary targets and secondary fluorescently labeled signal probes contained in the reaction mixture. This results in specific cleavage of the secondary signal probes by the Cleavase enzyme. Fluorescence signal is generated when this secondary probe, labeled with dye molecules capable of fluorescence resonance energy transfer, is cleaved. Cleavases have stringent requirements relative to the structure formed by the overlapping DNA sequences or flaps and can, therefore, be used to specifically detect single base pair mismatches immediately upstream of the cleavage site on the downstream DNA strand. See Ryan D et al. *Molecular Diagnosis* Vol. 4 No 2 1999:135-144 and Lyamichev V et al. *Nature Biotechnology* Vol 17 1999:292-296, see also U.S. Pat. Nos. 5,846,717 and 6,001,567 (the disclosures of which are incorporated herein by reference in their entirety).

In some embodiments, a composition contains two or more differently labeled genotyping oligonucleotides for simultaneously probing the identity of nucleotides at two or more polymorphic sites. It is also contemplated that primer compositions may contain two or more sets of allele-specific primer pairs to allow simultaneous targeting and amplification of two or more regions containing a polymorphic site.

CNTF genotyping oligonucleotides of the invention may also be immobilized on or synthesized on a solid surface such as a microchip, bead or glass slide (see, e.g., WO 98/20020 and WO 98/20019). Such immobilized genotyping oligonucleotides may be used in a variety of polymorphism detection assays, including but not limited to probe hybridization and polymerase extension assays. Immobilized CNTF genotyping oligonucleotides of the invention may comprise an ordered array of oligonucleotides designed to rapidly screen a DNA sample for polymorphisms in multiple genes at the same time.

An allele-specific oligonucleotide primer of the invention has a 3' terminal nucleotide, or preferably a 3' penultimate nucleotide, that is complementary to only one nucleotide of a particular SNP, thereby acting as a primer for polymerase-mediated extension only if the allele containing that nucleotide is present. Allele-specific oligonucleotide (ASO) primers hybridizing to either the coding or noncoding strand are contemplated by the invention. An ASO primer for detecting CNTF gene polymorphisms could be developed using techniques known to those of skill in the art.

Other genotyping oligonucleotides of the invention hybridize to a target region located one to several nucleotides downstream of one of the novel polymorphic sites identified herein. Such oligonucleotides are useful in polymerase-mediated primer extension methods for detecting one of the novel polymorphisms described herein and therefore such genotyping oligonucleotides are referred to herein as "primer-extension oligonucleotides". In a preferred embodiment, the 3'-terminus of a primer-extension oligonucleotide is a deoxynucleotide complementary to the nucleotide located immediately adjacent to the polymorphic site.

In another embodiment, the invention provides a kit comprising at least two genotyping oligonucleotides packaged in separate containers. The kit may also contain other components such as hybridization buffer (where the oligonucleotides are to be used as a probe) packaged in a separate container. Alternatively, where the oligonucleotides are to be used to amplify a target region, the kit may contain, packaged in separate containers, a polymerase and a reaction buffer optimized for primer extension mediated by the polymerase, such as PCR.

The above described oligonucleotide compositions and kits are useful in methods for genotyping and/or haplotyping the CNTF gene in an individual. As used herein, the terms "CNTF genotype" and "CNTF haplotype" mean the genotype or haplotype containing the nucleotide pair or nucleotide, respectively, that is present at one or more of the novel polymorphic sites described herein and may optionally also include the nucleotide pair or nucleotide present at one or more additional polymorphic sites in the CNTF gene. The additional polymorphic sites may be currently known polymorphic sites or sites that are subsequently discovered.

One embodiment of the genotyping method involves isolating from the individual a nucleic acid mixture comprising the two copies of the CNTF gene, or a fragment thereof, that are present in the individual, and determining the identity of the nucleotide pair at one or more of the polymorphic sites in the two copies to assign a CNTF genotype to the individual. As will be readily understood by the skilled artisan, the two "copies" of a gene in an individual may be the same allele or may be different alleles. In a particularly preferred embodiment, the genotyping method comprises determining the identity of the nucleotide pair at each polymorphic site.

Typically, the nucleic acid mixture or protein is isolated from a biological sample taken from the individual, such as a blood sample or tissue sample. Suitable tissue samples include whole blood, semen, saliva, tears, urine, fecal material, sweat, buccal smears, skin, and biopsies of specific organ tissues such as muscle or nerve tissue and hair. The nucleic acid mixture may be comprised of genomic DNA, mRNA, or cDNA and, in the latter two cases, the biological sample must be obtained from an organ in which the CNTF gene is expressed. Furthermore it will be understood by the skilled artisan that mRNA or cDNA preparations would not be used to detect polymorphisms located in introns or in 5' and 3' nontranscribed regions. If a CNTF gene fragment is isolated, it must contain the polymorphic site(s) to be genotyped.

One embodiment of the haplotyping method comprises isolating from the individual a nucleic acid molecule containing only one of the two copies of the CNTF gene, or a fragment thereof, that is present in the individual and determining in that copy the identity of the nucleotide at one or more of the polymorphic sites in that copy to assign a CNTF haplotype to the individual. The nucleic acid may be isolated using any method capable of separating the two copies of the CNTF gene or fragment, including but not limited to, one of the methods described above for preparing CNTF isogenes, with targeted in vivo cloning being the preferred approach.

As will be readily appreciated by those skilled in the art, any individual clone will only provide haplotype information on one of the two CNTF gene copies present in an individual. If haplotype information is desired for the individual's other copy, additional CNTF clones will need to be examined. Typically, at least five clones should be examined to have more than a 90% probability of haplotyping both copies of the CNTF gene in an individual. In a particularly preferred embodiment, the nucleotide at each of polymorphic site is identified.

In a preferred embodiment, a CNTF haplotype pair is determined for an individual by identifying the phased sequence of nucleotides at one or more of the polymorphic sites in each copy of the CNTF gene that is present in the individual. In a particularly preferred embodiment, the haplotyping method comprises identifying the phased sequence of nucleotides at each polymorphic site in each copy of the CNTF gene. When haplotyping both copies of the gene, the identifying step is preferably performed with each copy of the gene being placed in separate containers. However, it is also envisioned that if the two copies are labeled with different tags, or are otherwise separately distinguishable or identifiable, it could be possible in some cases to perform the method in the same container. For example, if first and second copies of the gene are labeled with different first and second fluorescent dyes, respectively, and an allele-specific oligonucleotide labeled with yet a third different fluorescent dye is used to assay the polymorphic site(s), then detecting a combination of the first and third dyes would identify the polymorphism in the first gene copy while detecting a combination of the second and third dyes would identify the polymorphism in the second gene copy.

In both, the genotyping and haplotyping methods, the identity of a nucleotide (or nucleotide pair) at a polymorphic site(s) may be determined by amplifying a target region(s) containing the polymorphic site(s) directly from one or both copies of the CNTF gene, or fragment thereof, and the sequence of the amplified region(s) determined by conventional methods. It will be readily appreciated by the skilled artisan that only one nucleotide will be detected at a polymorphic site in individuals who are homozygous at that site, while two different nucleotides will be detected if the individual is heterozygous for that site. The polymorphism may be identified directly, known as positive-type identification, or by inference, referred to as negative-type identification. For example, where a SNP is known to be guanine and cytosine in a reference population, a site may be positively determined to be either guanine or cytosine for all individual homozygous at that site, or both guanine and cytosine, if the individual is heterozygous at that site. Alternatively, the site may be negatively determined to be not guanine (and thus cytosine/cytosine) or not cytosine (and thus guanine/guanine).

In addition, the identity of the allele(s) present at any of the novel polymorphic sites described herein may be indirectly determined by genotyping a polymorphic site not disclosed herein that is in linkage disequilibrium with the polymorphic site that is of interest. Two sites are said to be in linkage disequilibrium if the presence of a particular variant at one site enhances the predictability of another variant at the second site (See, Stevens, J C 1999, *Mol Diag* 4:309-317). Polymorphic sites in linkage disequilibrium with the presently disclosed polymorphic sites may be located in regions of the gene or in other genomic regions not examined herein. Genotyping of a polymorphic site in linkage disequilibrium with the novel polymorphic sites described herein may be performed by, but is not limited to, any of the above-mentioned methods for detecting the identity of the allele at a polymorphic site.

The target region(s) may be amplified using any oligonucleotide-directed amplification method, including but not limited to polymerase chain reaction (PCR) (U.S. Pat. No. 4,965,188), ligase chain reaction (LCR) (Barany et al., Proc Natl Acad Sci USA 88:189-193, 1991; WO 90/01069), and oligonucleotide ligation assay (OLA) (Landegren et al., Science 241:1077-1080, 1988). Oligonucleotides useful as primers or probes in such methods should specifically hybridize to a region of the nucleic acid that contains or is adjacent to the polymorphic site. Typically, the oligonucleotides are between 10 and 35 nucleotides in length and preferably, between 15 and 30 nucleotides in length. Most preferably, the oligonucleotides are 20 to 25 nucleotides long. The exact length of the oligonucleotide will depend on many factors that are routinely considered and practiced by the skilled artisan.

Other known nucleic acid amplification procedures may be used to amplify the target region including transcription-based amplification systems (U.S. Pat. No. 5,130,238; EP 329,822; U.S. Pat. No. 5,169,766, WO 89/06700) and isothermal methods (Walker et al., *Proc Natl Acad Sci USA* 89:392-396, 1992).

A polymorphism in the target region may also be assayed before or after amplification using one of several hybridization-based methods known in the art. Typically, allele-specific oligonucleotides are utilized in performing such methods. The allele-specific oligonucleotides may be used as differently labeled probe pairs, with one member of the pair showing a perfect match to one variant of a target sequence and the other member showing a perfect match to a different variant. In some embodiments, more than one polymorphic site may be detected at once using a set of allele-specific oligonucleotides or oligonucleotide pairs. Preferably, the members of the set have melting temperatures within 5° C.

and more preferably within 2° C., of each other when hybridizing to each of the polymorphic sites being detected.

Hybridization of an allele-specific oligonucleotide to a target polynucleotide may be performed with both entities in solution or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Allele-specific oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid.

The genotype or haplotype for the CNTF gene of an individual may also be determined by hybridization of a nucleic sample containing one or both copies of the gene to nucleic acid arrays and subarrays such as described in WO 95/11995. The arrays would contain a battery of allele-specific oligonucleotides representing each of the polymorphic sites to be included in the genotype or haplotype.

The identity of polymorphisms may also be determined using a mismatch detection technique, including but not limited to the RNase protection method using riboprobes (Winter et al., Proc Natl Acad Sci USA 82:7575, 1985; Meyers et al., Science 230:1242, 1985) and proteins which recognize nucleotide mismatches, such as the *E. coli* mutS protein (Modrich P. Ann Rev Genet 25:229-253, 1991). Alternatively, variant alleles can be identified by single strand conformation polymorphism (SSCP) analysis (Orita et al., Genomics 5:874-879, 1989; Humphries et al., in Molecular Diagnosis of Genetic Diseases, R. Elles, ed., pp. 321-340, 1996) or denaturing gradient gel electrophoresis (DGGE) (Wartell et at., Nucl Acids Res 18:2699-2706, 1990; Sheffield et al., Proc Natl Acad Sci USA 86:232-236, 1989).

A polymerase-mediated primer extension method may also be used to identify the polymorphism(s). Several such methods have been described in the patent and scientific literature and include the "Genetic Bit Analysis" method (WO 92/15712) and the ligase/polymerase mediated genetic bit analysis (U.S. Pat. No. 5,679,524). Related methods are disclosed in WO 91/02087, WO 90/09455, WO 95/17676, U.S. Pat. Nos. 5,302,509 and 5,945,283. Extended primers containing a polymorphism may be detected by mass spectrometry as described in U.S. Pat. No. 5,605,798. Another primer extension method is allele-specific PCR (Ruafio et al., Nucl Acids Res 17:8392, 1989; Ruafio et al., Nucl Acids Res 19, 6877-6882, 1991; WO 93/22456; Turki et al., I Clin Invest 95:1635-1641, 1995). In addition, multiple polymorphic sites may be investigated by simultaneously amplifying multiple regions of the nucleic acid using sets of allele-specific primers as described in Wallace et al. (WO 89/10414).

In a preferred embodiment, the haplotype frequency data for each ethnogeographic group is examined to determine whether it is consistent with Hardy-Weinberg equilibrium. Hardy-Weinberg equilibrium (D. L. Hartl et al., Principles of Population Genomics, Sinauer Associates (Sunderland, Mass.), 3rd Ed., 1997) postulates that the frequency of finding the haplotype pair $H_1/H_2$ is equal to $P_{H-W}(H_1/H_2)=2p(H_1)p(H_2)$ if $H_1 \neq H_2$ and $P_{H-W}(H_1/H_2)=p(H_1)p(H_2)$ if $H_1=H_2$. A statistically significant difference between the observed and expected haplotype frequencies could be due to one or more factors including significant inbreeding in the population group, strong selective pressure on the gene, sampling bias, and/or errors in the genotyping process. If large deviations from Hardy-Weinberg equilibrium are observed in an ethnogeographic group, the number of individuals in that group can be increased to see if the deviation is due to a sampling bias. If a larger sample size does not reduce the difference between observed and expected haplotype pair frequencies, then one may wish to consider haplotyping the individual using a direct haplotyping method such as, for example, CLASPER System™ technology (U.S. Pat. No. 5,866,404), or allele-specific long-range PCR (Michalotos-Beloin et al., Nucl Acids Res 24:4841-4843, 1996).

In one embodiment of this method for predicting a CNTF haplotype pair, the assigning step involves performing the following analysis. First, each of the possible haplotype pairs is compared to the haplotype pairs in the reference population. Generally, only one of the haplotype pairs in the reference population matches a possible haplotype pair and that pair is assigned to the individual. Occasionally, only one haplotype represented in the reference haplotype pairs is consistent with a possible haplotype pair for an individual, and in such cases the individual is assigned a haplotype pair containing this known haplotype and a new haplotype derived by subtracting the known haplotype from the possible haplotype pair. In rare cases, either no haplotype in the reference population are consistent with the possible haplotype pairs, or alternatively, multiple reference haplotype pairs are consistent with the possible haplotype pairs. In such cases, the individual is preferably haplotyped using a direct molecular haplotyping method such as, for example, CLASPER System™ technology (U.S. Pat. No. 5,866,404), or allele-specific long-range PCR (Michalotos-Beloin et al., Nucl Acids Res 24:4841-4843, 1996).

The invention also provides a method for determining the frequency of a CNTF genotype or CNTF haplotype in a population. The method comprises determining the genotype or the haplotype pair for the CNTF gene that is present in each member of the population, wherein the genotype or haplotype comprises the nucleotide pair or nucleotide detected at one or more of the polymorphic sites in the CNTF gene, including but not limited to the FS63 TER polymorphism; and calculating the frequency any particular genotype or haplotype is found in the population. The population may be a reference population, a family population, a same sex population, a population group, a trait population (e.g., a group of individuals exhibiting a trait of interest such as a medical condition or response to a therapeutic treatment).

In another aspect of the invention, frequency data for CNTF genotypes and/or haplotypes found in a reference population are used in a method for identifying an association between a trait and a CNTF genotype or a CNTF haplotype. The trait may be any detectable phenotype, including but not limited to susceptibility to a disease or response to a treatment. The method involves obtaining data on the frequency of the genotype(s) or haplotype(s) of interest in a reference population as well as in a population exhibiting the trait. Frequency data for one or both of the reference and trait populations may be obtained by genotyping or haplotyping each individual in the populations using one of the methods described above. The haplotypes for the trait population may be determined directly or, alternatively, by the predictive genotype to haplotype approach described above.

In another embodiment, the frequency data for the reference and/or trait populations is obtained by accessing previously determined frequency data, which may be in written or electronic form. For example, the frequency data may be present in a database that is accessible by a computer. Once the frequency data is obtained the frequencies of the genotype (s) or haplotype(s) of interest in the reference and trait populations are compared. In a preferred embodiment, the frequencies of all genotypes and/or haplotypes observed in the populations are compared. If a particular genotype or haplotype for the CNTF gene is more frequent in the trait population than in the reference population at a statistically significant amount, then the trait is predicted to be associated with that CNTF genotype or haplotype.

In a preferred embodiment statistical analysis is performed by the use of standard analysis of variation (ANOVA) tests with a Bonferoni correction and/or a bootstrapping method that simulates the genotype phenotype correlation many times and calculates a significance value. When many polymorphisms are being analyzed a correction to factor may be performed to correct for a significant association that might be found by chance. For statistical methods for use in the methods of this invention, see: Statistical Methods in Biology, $3^{rd}$ edition, Bailey NTJ, Cambridge Univ. Press (1997); Introduction to Computational Biology, Waterman Miss., CRC Press (2000), and Bioinformatics, Baxevanis AD and Ouellette BFF editors (2001) John Wiley & Sons, Inc.

In a preferred embodiment of the method, the trait of interest is a clinical response exhibited by a patient to some therapeutic treatment, for example, response to a drug targeting CNTF or response to a therapeutic treatment for a medical condition.

In another embodiment of the invention, a detectable genotype or haplotype that is in linkage disequilibrium with the CNTF genotype or haplotype of interest may be used as a surrogate marker. A genotype that is in linkage disequilibrium with a CNTF genotype may be discovered by determining if a particular genotype or haplotype for the CNTF gene is more frequent in the population that also demonstrates the potential surrogate marker genotype than in the reference population at a statistically significant amount, then the marker genotype is predicted to be associated with that CNTF genotype or haplotype and then can be used as a surrogate marker in place of the CNTF genotype.

As used herein, "medical condition" includes but is not limited to any condition or disease manifested as one or more physical and/or psychological symptoms for which treatment is desirable, and includes previously and newly identified diseases and other disorders.

As used herein, the term "clinical response" means any or all of the following: a quantitative measure of the response, no response, and adverse response (i.e., side effects).

In order to deduce a correlation between clinical response to a treatment and a CNTF genotype or haplotype, it is necessary to obtain data on the clinical responses exhibited by a population of individuals who received the treatment, hereinafter the "clinical population". This clinical data may be obtained by analyzing the results of a clinical trial that has already been run and/or the clinical data may be obtained by designing and carrying out one or more new clinical trials.

As used herein, the term "clinical trial" means any research study designed to collect clinical data on responses to a particular treatment, and includes but is not limited to phase I, phase II and phase III clinical trials. Standard methods are used to define the patient population and to enroll subjects.

It is preferred that the individuals included in the clinical population have been graded for the existence of the medical condition of interest. This is important in cases where the symptom(s) being presented by the patients can be caused by more than one underlying condition, and where treatment of the underlying conditions are not the same. An example of this would be where patients experience breathing difficulties that are due to either asthma or respiratory infections. If both sets were treated with an asthma medication, there would be a spurious group of apparent non-responders that did not actually have asthma. These people would affect the ability to detect any correlation between haplotype and treatment outcome. This grading of potential patients could employ a standard physical exam or one or more lab tests. Alternatively, grading of patients could use haplotyping for situations where there is a strong correlation between haplotype pair and disease susceptibility or severity.

The therapeutic treatment of interest is administered to each individual in the trial population and each individual's response to the treatment is measured using one or more predetermined criteria. It is contemplated that in many cases, the trial population will exhibit a range of responses and that the investigator will choose the number of responder groups (e.g., low, medium, high) made up by the various responses. In addition, the CNTF gene for each individual in the trial population is genotyped and/or haplotyped, which may be done before or after administering the treatment.

After both the clinical and polymorphism data have been obtained, correlations between individual response and CNTF genotype or haplotype content are created. Correlations may be produced in several ways. In one method, individuals are grouped by their CNTF genotype or haplotype (or haplotype pair) (also referred to as a polymorphism group), and then the averages and standard deviations of clinical responses exhibited by the members of each polymorphism group are calculated.

These results are then analyzed to determine if any observed variation in clinical response between polymorphism groups is statistically significant. Statistical analysis methods which may be used are described in L. D. Fisher and G. vanBelle, "Biostatistics: A Methodology for the Health Sciences", Wiley-Interscience (New York) 1993. This analysis may also include a regression calculation of which polymorphic sites in the CNTF gene give the most significant contribution to the differences in phenotype. One regression model useful in the invention is described in the PCT Application entitled "Methods for Obtaining and Using Haplotype Data", filed Jun. 26, 2000.

A second method for finding correlations between CNTF haplotype content and clinical responses uses predictive models based on error-minimizing optimization algorithms. One of many possible optimization algorithms is a genetic algorithm (R. Judson, "Genetic Algorithms and Their Uses in Chemistry" in Reviews in Computational Chemistry, Vol. 10, pp. 1-73, K. B. Lipkowitz and D. B. Boyd, eds. (VCH Publishers, New York, 1997). Simulated annealing (Press et al., "Numerical Recipes in C: The Art of Scientific Computing", Cambridge University Press (Cambridge) 1992, Ch. 10), neural networks (E. Rich and K. Knight, "Artificial Intelligence", 2nd Edition (McGraw-Hill, New York, 1991, Ch. 18), standard gradient descent methods (Press et al., supra Ch. 10), or other global or local optimization approaches (see discussion in Judson, supra) could also be used. Preferably, the correlation is found using a genetic algorithm approach as described in PCT Application entitled "Methods for Obtaining and Using Haplotype Data", filed Jun. 26, 2000.

Correlations may also be analyzed using ANOVA techniques to determine how much of the variation in the clinical data is explained by different subsets of the polymorphic sites in the CNTF gene. As described in PCT Application entitled "Methods for Obtaining and Using Haplotype Data", filed Jun. 26, 2000, ANOVA is used to test hypotheses about whether a response variable is caused by or correlated with one or more traits or variables that can be measured (Fisher and vanBelle, supra, Ch. 10).

From the analyses described above, a mathematical model may be readily constructed by the skilled artisan that predicts clinical response as a function of CNTF genotype or haplotype content. Preferably, the model is validated in one or more follow-up clinical trials designed to test the model.

The identification of an association between a clinical response and a genotype or haplotype (or haplotype pair) for the CNTF gene may be the basis for designing a diagnostic method to determine those individuals who will or will not respond to the treatment, or alternatively, will respond at a lower level and thus may require more treatment, i.e., a greater dose of a drug. The diagnostic method may take one of several forms: for example, a direct DNA test (i.e., genotyping or haplotyping one or more of the polymorphic sites in the CNTF gene), a serological test, or a physical exam measurement. The only requirement is that there be a good correlation between the diagnostic test results and the underlying CNTF genotype or haplotype that is in turn correlated with the clinical response. In a preferred embodiment, this diagnostic method uses the predictive haplotyping method described above.

A computer may implement any or all analytical and mathematical operations involved in practicing the methods of the present invention. In addition, the computer may execute a program that generates views (or screens) displayed on a display device and with which the user can interact to view and analyze large amounts of information relating to the CNTF gene and its genomic variation, including chromosome location, gene structure, and gene family, gene expression data, polymorphism data, genetic sequence data, and clinical data population data (e.g., data on ethnogeographic origin, clinical responses, genotypes, and haplotypes for one or more populations). The CNTF polymorphism data described herein may be stored as part of a relational database (e.g., an instance of an Oracle database or a set of ASCII flat files). These polymorphism data may be stored on the computer's hard drive or may, for example, be stored on a CD-ROM or on one or more other storage devices accessible by the computer. For example, the data may be stored on one or more databases in communication with the computer via a network.

In other embodiments, the invention provides methods, compositions, and kits for haplotyping and/or genotyping the CNTF gene in an individual. The methods involve identifying the nucleotide or nucleotide pair present at nucleotide: 103 G>A in GenBank accession number X55890 (Version 1). This nucleotide substitution results in the creation of a new splice acceptor site and a resultant aberrant protein. See, PubMed ID # 9285965.

The compositions contain oligonucleotide probes and primers designed to specifically hybridize to one or more target regions containing, or that are adjacent to, a polymorphic site. The methods and compositions for establishing the genotype or haplotype of an individual at the novel polymorphic sites described herein are useful for studying the effect of the polymorphisms in the etiology of diseases affected by the expression and function of the CNTF protein or lack thereof, studying the efficacy of drugs targeting CNTF, predicting individual susceptibility to diseases affected by the expression and function of the CNTF protein and predicting individual responsiveness to drugs targeting CNTF.

In yet another embodiment, the invention provides a method for identifying an association between a genotype or haplotype and a trait. In preferred embodiments, the trait is susceptibility to a disease, severity of a disease, the staging of a disease or response to a drug. Such methods have applicability in developing diagnostic tests and therapeutic treatments for all pharmacogenetic applications where there is the potential for an association between a genotype and a treatment outcome including efficacy measurements, pharmacokinetic (PK) measurements and side effect measurements.

The present invention also provides a computer system for storing and displaying polymorphism data determined for the CNTF gene. The computer system comprises a computer processing unit; a display; and a database containing the polymorphism data. The polymorphism data includes the polymorphisms, the genotypes and the haplotypes identified for the CNTF gene in a reference population. In a preferred embodiment, the computer system is capable of producing a display showing CNTF haplotypes organized according to their evolutionary relationships.

In another aspect, the invention provides SNP probes, which are useful in classifying people according to their types of genetic variation. The SNP probes according to the invention are oligonucleotides, which can discriminate between alleles of a SNP nucleic acid in conventional allelic discrimination assays.

As used herein, a "SNP nucleic acid" is a nucleic acid sequence, which comprises a nucleotide that is variable within an otherwise identical nucleotide sequence between individuals or groups of individuals, thus, existing as alleles. Such SNP nucleic acids are preferably from about 15 to about 500 nucleotides in length. The SNP nucleic acids may be part of a chromosome, or they may be an exact copy of a part of a chromosome, e.g., by amplification of such a part of a chromosome through PCR or through cloning. The SNP nucleic acids are referred to hereafter simply as "SNPs". The SNP probes according to the invention are oligonucleotides that are complementary to a SNP nucleic acid.

As used herein, the term "complementary" means exactly complementary throughout the length of the oligonucleotide in the Watson and Crick sense of the word.

In certain preferred embodiments, the oligonucleotides according to this aspect of the invention are complementary to one allele of the SNP nucleic acid, but not to any other allele of the SNP nucleic acid. Oligonucleotides according to this embodiment of the invention can discriminate between alleles of the SNP nucleic acid in various ways. For example, under stringent hybridization conditions, an oligonucleotide of appropriate length will hybridize to one allele of the SNP nucleic acid, but not to any other allele of the SNP nucleic acid. The oligonucleotide may be labeled by a radiolabel or a fluorescent label. Alternatively, an oligonucleotide of appropriate length can be used as a primer for PCR, wherein the 3' terminal nucleotide is complementary to one allele of the SNP nucleic acid, but not to any other allele. In this embodiment, the presence or absence of amplification by PCR determines the haplotype of the SNP nucleic acid.

Thus, in one embodiment, the invention provides an isolated polynucleotide comprising a nucleotide sequence that is a polymorphic variant of a reference sequence for the CNTF gene or a fragment thereof. The reference sequence comprises GenBank accession No. X55890 (Version 1) and the polymorphic variant comprise at least one polymorphism, including but not limited to nucleotide: 103 G>A. A particularly preferred polymorphic variant is a naturally occurring isoform (also referred to herein as an "isogene") of the CNTF gene.

Genomic and cDNA fragments of the invention comprise at least one novel polymorphic site identified herein and have a length of at least 10 nucleotides and may range up to the full length of the gene. Preferably, a fragment according to the present invention is between 100 and 3000 nucleotides in length, and more preferably between 200 and 2000 nucleotides in length, and most preferably between 500 and 1000 nucleotides in length.

In describing the polymorphic sites identified herein reference is made to the sense strand of the gene for convenience. However, as recognized by the skilled artisan, nucleic acid molecules containing the CNTF gene may be complementary double stranded molecules and thus, reference to a particular site on the sense strand refers as well to the corresponding site on the complementary antisense strand. Thus, reference may be made to the same polymorphic site on either strand and an oligonucleotide may be designed to hybridize specifically to either strand at a target region containing the polymorphic site. Thus, the invention also includes single-stranded polynucleotides that are complementary to the sense strand of the CNTF genomic variants described herein.

Effect(s) of the polymorphisms identified herein on expression of CNTF may be investigated by preparing recombinant cells and/or organisms, preferably recombinant animals, containing a polymorphic variant of the CNTF gene. As used herein, "expression" includes but is not limited to one or more of the following: transcription of the gene into precursor mRNA; splicing and other processing of the precursor mRNA to produce mature mRNA; mRNA stability; translation of the mature mRNA into CTNF protein (including codon usage and tRNA availability); and glycosylation and/or other modifications of the translation product, if required for proper expression and function.

To prepare a recombinant cell of the invention, the desired CNTF isogene may be introduced into the cell in a vector such that the isogene remains extrachromosomal. In such a situation, the gene will be expressed by the cell from the extrachromosomal location. In a preferred embodiment, the CNTF isogene is introduced into a cell in such a way that it recombines with the endogenous CNTF gene present in the cell. Such recombination requires the occurrence of a double recombination event, thereby resulting in the desired CNTF gene polymorphism. Vectors for the introduction of genes both for recombination and for extrachromosomal maintenance are known in the art, and any suitable vector or vector construct may be used in the invention. Methods such as electroporation, particle bombardment, calcium phosphate co-precipitation and viral transduction for introducing DNA into cells are known in the art; therefore, the choice of method may lie with the competence and preference of the skilled practitioner.

Examples of cells into which the CNTF isogene may be introduced include, but are not limited to, continuous culture cells, such as COS, NIH/3T3, and primary or culture cells of the relevant tissue type, i.e., they express the CNTF isogene. Such recombinant cells can be used to compare the biological activities of the different protein variants.

Recombinant organisms, i.e., transgenic animals, expressing a variant gene are prepared using standard procedures known in the art. Preferably, a construct comprising the variant gene is introduced into a nonhuman animal or an ancestor of the animal at an embryonic stage, i.e., the one-cell stage, or generally not later than about the eight-cell stage. Transgenic animals carrying the constructs of the invention can be made by several methods known to those having skill in the art. One method involves transfecting into the embryo a retrovirus constructed to contain one or more insulator elements, a gene or genes of interest, and other components known to those skilled in the art to provide a complete shuttle vector harboring the insulated gene(s) as a transgene, see e.g., U.S. Pat. No. 5,610,053. Another method involves directly injecting a transgene into the embryo. A third method involves the use of embryonic stem cells.

Examples of animals, into which the CNTF isogenes may be introduced include, but are not limited to, mice, rats, other rodents, and nonhuman primates (see "The Introduction of Foreign Genes into Mice" and the cited references therein, In: Recombinant DNA, Eds. J. D. Watson, M. Gilman, J. Witkowski, and M. Zoller; W.H. Freeman and Company, New York, pages 254-272). Transgenic animals stably expressing a human CNTF isogene and producing human CNTF protein can be used as biological models for studying diseases related to abnormal CNTF expression and/or activity, and for screening and assaying various candidate drugs, compounds, and treatment regimens to reduce the symptoms or effects of these diseases.

It will be understood by the skilled reader that most or all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

Many of the compounds used in this invention are amines, and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like.

Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, .beta.-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid, oxalic acid or fumaric acid.

Administration

The dosages of the drugs used in the present invention must, in the final analysis, be set by the physician in charge of the case, using knowledge of the drugs, the properties of the drugs in combination as determined in clinical trials, and the characteristics of the patient, including diseases other than that for which the physician is treating the patient. General outlines of the dosages, and some preferred dosages, can and will be provided here, for example; Iloperidone: from 1 to 50 mg once per day and most preferred from 12 to 16 mg once per day; Olanzapine: from about 0.25 to 50 mg, once/day;

preferred, from 1 to 30 mg, once/day; and most preferably 1 to 25 mg once/day; Clozapine: from about 12.5 to 900 mg daily; preferred, from about 150 to 450 mg daily; Risperidone: from about 0.25 to 16 mg daily; preferred from about 2-8 mg daily; Sertindole: from about 0.0001 to 1.0 mg/kg daily; Quetiapine: from about 1.0 to 40 mg/kg given once daily or in divided doses; Ziprasidone: from about 5 to 500 mg daily; preferred from about 50 to 100 mg daily; Haldol: from 0.5 to 40 mg once per day.

All of the compounds concerned are orally available and are normally administered orally, and so oral administration of the adjunctive combination is preferred. They may be administered together, in a single dosage form, or may be administered separately. However, oral administration is not the only route or even the only preferred route. For example, transdermal administration may be very desirable for patients who are forgetful or petulant about taking oral medicine. One of the drugs may be administered by one route, such as oral, and the others may be administered by the transdermal, percutaneous, intravenous, intramuscular, intranasal or intrarectal route, in particular circumstances. The route of administration may be varied in any way, limited by the physical properties of the drugs and the convenience of the patient and the caregiver.

Transcriptional State Measurement

Preferably, measurement of the transcriptional state is made by hybridization to transcript arrays, which are described in this subsection. Certain other methods of transcriptional state measurement are described later in this subsection.

Transcript Arrays Generally

In one embodiment of the present invention, use is made of "transcript arrays" (also called herein "microarrays"). Transcript arrays can be employed for analyzing the transcriptional state in a cell.

In one embodiment, transcript arrays are produced by hybridizing detectably labeled polynucleotides representing the mRNA transcripts present in a cell (e.g., fluorescently labeled cDNA synthesized from total cell mRNA) to a microarray. A microarray is a surface with an ordered array of binding (e.g., hybridization) sites for products of many of the genes in the genome of a cell or organism, preferably most or almost all of the genes. Microarrays can be made in a number of ways, of which several are described below. However produced, microarrays share certain characteristics: The arrays are reproducible, allowing multiple copies of a given array to be produced and easily compared with each other. Preferably the microarrays are small, usually smaller than 5 cm$^2$, and they are made from materials that are stable under binding (e.g. nucleic acid hybridization) conditions. A given binding site or unique set of binding sites in the microarray will specifically bind the product of a single gene in the cell. Although there may be more than one physical binding site (hereinafter "site") per specific mRNA, for the sake of clarity the discussion below will assume that there is a single site. In a specific embodiment, positionally addressable arrays containing affixed nucleic acids of known sequence at each location are used.

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

Preparation of Microarrays

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid analogue to which a particular cognate cDNA can specifically hybridize. The nucleic acid or analogue of the binding site can be, e.g., a synthetic oligomer, a full-length cDNA, a less-than full-length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often at least about 75%, more often at least about 85%, even more often more than about 90%, and most often at least about 99%. Preferably, the microarray has binding sites for genes relevant to testing and confirming a biological network model of interest.

A "gene" is identified as an open reading frame (ORF) of preferably at least 50, 75, or 99 amino acids from which a messenger RNA is transcribed in the organism (e.g., if a single cell) or in some cell in a multicellular organism. The number of genes in a genome can be estimated from the number of mRNAs expressed by the organism, or by extrapolation from a well-characterized portion of the genome. When the genome of the organism of interest has been sequenced, the number of ORFs can be determined and mRNA coding regions identified by analysis of the DNA sequence. For example, the *Saccharomyces cerevisiae* genome has been completely sequenced and is reported to have approximately 6275 open reading frames (ORFS) longer than 99 amino acids. Analysis of these ORFs indicates that there are 5885 ORFs that are likely to specify protein products (Goffeau et al., 1996, Life with 6000 genes, *Science* 274:546-567, which is incorporated by reference in its entirety for all purposes). In contrast, the human genome is estimated to contain approximately 100,000 genes.

Preparing Nucleic Acids for Microarrays

As noted above, the "binding site" to which a particular cognate cDNA specifically hybridizes is usually a nucleic acid or nucleic acid analogue attached at that binding site. In one embodiment, the binding sites of the microarray are DNA polynucleotides corresponding to at least a portion of each gene in an organism's genome. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, that result in amplification of unique fragments (i.e. fragments that do not share more than 10 bases of contiguous identical sequence with any other fragment on the microarray). Computer programs are useful in the design of primers with the required specificity and optimal amplification properties. See, e.g., Oligo pl version 5.0 (National Biosciences). In the case of binding sites corresponding to very long genes, it will sometimes be desirable to amplify segments near the 3' end of the gene so that when oligo-dT primed cDNA probes are hybridized to the microarray; less-than-full length probes will bind efficiently. Typically each gene fragment on the microarray will be between about 50 bp and about 2000 bp, more typically between about 100 bp and about 1000 bp, and usually between about 300 bp and about 800 bp in length. PCR methods are well known and are described, for example, in Innis et al. eds., 1990, PCR Protocols: A Guide to Methods and Applications, Academic Press Inc. San Diego, Calif., which is incorporated by reference in its entirety for all purposes. It will be apparent that computer controlled robotic systems are useful for isolating and amplifying nucleic acids.

An alternative means for generating the nucleic acid for the microarray is by synthesis of synthetic polynucleotides or oligonucleotides, e.g., using N-phosphonate or phosphoramidite chemistries (Froehler et al., 1986, *Nucleic Acid Res* 14:5399-5407; McBride et al., 1983, *Tetrahedron Lett.* 24:245-248). Synthetic sequences are between about 15 and about 500 bases in length, more typically between about 20 and about 50 bases. In some embodiments, synthetic nucleic acids include non-natural bases, e.g., inosine. As noted above, nucleic acid analogues may be used as binding sites for hybridization. An example of a suitable nucleic acid analogue is peptide nucleic acid (see, e.g., Egholm et al., 1993, PNA hybridizes to complementary oligonucleotides obeying the Watson-Crick hydrogen-bonding rules, *Nature* 365:566-568; see also U.S. Pat. No. 5,539,083).

In an alternative embodiment, the binding (hybridization) sites are made from plasmid or phage clones of genes, cDNAs (e.g., expressed sequence tags), or inserts therefrom (Nguyen et al., 1995, Differential gene expression in the murine thymus assayed by quantitative hybridization of arrayed cDNA clones, *Genomics* 29:207-209). In yet another embodiment, the polynucleotide of the binding sites is RNA.

Attaching Nucleic Acids to the Solid Surface

The nucleic acid or analogue are attached to a solid support, which may be made from glass, plastic (e.g., polypropylene, nylon), polyacrylamide, nitrocellulose, or other materials. A preferred method for attaching the nucleic acids to a surface is by printing on glass plates, as is described generally by Schena et al., 1995, Quantitative monitoring of gene expression patterns with a complementary DNA microarray, *Science* 270:467-470. This method is especially useful for preparing microarrays of cDNA. See, also, DeRisi et al., 1996, Use of a cDNA microarray to analyze gene expression patterns in human cancer, *Nature Genetics* 14:457-460; Shalon et al., 1996, A DNA microarray system for analyzing complex DNA samples using two-color fluorescent probe hybridization, *Genome Res.* 6:639-645; and Schena et al., 1995, Parallel human genome analysis; microarray-based expression of 1000 genes, *Proc. Natl. Acad. Sci. USA* 93:10539-11286. Each of the aforementioned articles is incorporated by reference in its entirety for all purposes.

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Light-directed spatially addressable parallel chemical synthesis, *Science* 251: 767-773; Pease et al., 1994, Light-directed oligonucleotide arrays for rapid DNA sequence analysis, *Proc. Natl. Acad. Sci. USA* 91:5022-5026; Lockhart et al., 1996, Expression monitoring by hybridization to high-density oligonucleotide arrays, *Nature Biotech* 14:1675; U.S. Pat. Nos. 5,578,832; 5,556,752; and 5,510,270, each of which is incorporated by reference in its entirety for all purposes) or other methods for rapid synthesis and deposition of defined oligonucleotides (Blanchard et al., 1996, High-Density Oligonucleotide arrays, *Biosensors & Bioelectronics* 11: 687-90). When these methods are used, oligonucleotides (e.g., 20-mers) of known sequence are synthesized directly on a surface such as a derivatized glass slide. Usually, the array produced is redundant, with several oligonucleotide molecules per RNA. Oligonucleotide probes can be chosen to detect alternatively spliced mRNAs.

Other methods for making microarrays, e.g., by masking (Maskos and Southern, 1992, *Nuc. Acids Res.* 20:1679-1684), may also be used. In principal, any type of array, for example, dot blots on a nylon hybridization membrane (see Sambrook et al., Molecular Cloning—A Laboratory Manual (2nd Ed.), Vol. 1-3, Cold Spring Harbor Laboratory, Cold Spring Harbor, N.Y., 1989, which is incorporated in its entirety for all purposes), could be used, although, as will be recognized by those of skill in the art, very small arrays will be preferred because hybridization volumes will be smaller.

Generating Labeled Probes

Methods for preparing total and poly (A)+ RNA are well known and are described generally in Sambrook et al., supra. In one embodiment, RNA is extracted from cells of the various types of interest in this invention using guanidinium thiocyanate lysis followed by CsCl centrifugation (Chirgwin et al., 1979, *Biochemistry* 18:5294-5299). Poly (A)+ RNA is selected by selection with oligo-dT cellulose (see Sambrook et al., supra). Cells of interest include wild-type cells, drug-exposed wild-type cells, cells with modified/perturbed cellular constituent(s), and drug-exposed cells with modified/perturbed cellular constituent(s).

Labeled cDNA is prepared from mRNA by oligo dT-primed or random-primed reverse transcription, both of which are well known in the art (see e.g., Klug and Berger, 1987, *Methods Enzymol.* 152:316-325). Reverse transcription may be carried out in the presence of a dNTP conjugated to a detectable label, most preferably a fluorescently labeled dNTP. Alternatively, isolated mRNA can be converted to labeled antisense RNA synthesized by in vitro transcription of double-stranded cDNA in the presence of labeled dNTPs (Lockhart et al., 1996, Expression monitoring by hybridization to high-density oligonucleotide arrays, *Nature Biotech.* 14:1675, which is incorporated by reference in its entirety for all purposes). In alternative embodiments, the cDNA or RNA probe can be synthesized in the absence of detectable label and may be labeled subsequently, e.g., by incorporating biotinylated dNTPs or rNTP, or some similar means (e.g., photocross-linking a psoralen derivative of biotin to RNAs), followed by addition of labeled streptavidin (e.g., phycoerythrin-conjugated streptavidin) or the equivalent.

When fluorescently-labeled probes are used, many suitable fluorophores are known, including fluorescein, lissamine, phycoerythrin, rhodamine (Perkin Elmer Cetus), Cy2, Cy3, Cy3.5, Cy5, Cy5.5, Cy7, Fluor X (Amersham) and others (see, e.g., Kricka, 1992, Nonisotopic DNA Probe Techniques, Academic Press San Diego, Calif.). It will be appreciated that pairs of fluorophores are chosen that have distinct emission spectra so that they can be easily distinguished.

In another embodiment, a label other than a fluorescent label is used. For example, a radioactive label, or a pair of radioactive labels with distinct emission spectra, can be used (see Zhao et al., 1995, High density cDNA filter analysis: a novel approach for large-scale, quantitative analysis of gene expression, *Gene* 156:207; Pietu et al., 1996, Novel gene transcripts preferentially expressed in human muscles revealed by quantitative hybridization of a high density cDNA array, *Genome Res.* 6:492). However, because of scattering of radioactive particles, and the consequent requirement for widely spaced binding sites, use of radioisotopes is a less-preferred embodiment.

In one embodiment, labeled cDNA is synthesized by incubating a mixture containing 0.5 mM dGTP, dATP and dCTP plus 0.1 mM dTTP plus fluorescent deoxyribonucleotides (e.g., 0.1 mM Rhodamine 110 UTP (Perken Elmer Cetus) or 0.1 mM Cy3 dUTP (Amersham)) with reverse transcriptase (e.g., SuperScript.™. II, LTI Inc.) at 42° C. for 60 min.

Hybridization to Microarrays

Nucleic acid hybridization and wash conditions are chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., supra).

Optimal hybridization conditions will depend on the length (e.g., oligomer versus polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., 1987, Current Protocols in Molecular Biology, Greene Publishing and Wiley-Interscience, New York, which is incorporated in its entirety for all purposes. When the cDNA microarrays of Schena et al. are used, typical hybridization conditions are hybridization in 5×SSC plus 0.2% SDS at 65° C. for 4 hours followed by washes at 25° C. in low stringency wash buffer (1×SSC plus 0.2% SDS) followed by 10 minutes at 25° C. in high stringency wash buffer (0.1×SSC plus 0.2% SDS) (Shena et al., 1996, Proc. Natl. Acad. Sci. USA, 93:10614). Useful hybridization conditions are also provided in, e.g., Tijessen, 1993, Hybridization With Nucleic Acid Probes, Elsevier Science Publishers B. V. and Kricka, 1992, Nonisotopic DNA Probe Techniques, Academic Press San Diego, Calif.

Signal Detection and Data Analysis

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows specimen illumination at wavelengths specific to the fluorophores used and emissions from the fluorophore can be analyzed. In a preferred embodiment, the arrays are scanned with a laser fluorescent scanner with a computer controlled X-Y stage and a microscope objective. Sequential excitation of the fluorophore is achieved with a multi-line, mixed gas laser and the emitted light is split by wavelength and detected with a photomultiplier tube. Fluorescence laser scanning devices are described in Schena et al., 1996, *Genome Res.* 6:639-645 and in other references cited herein. Alternatively, the fiber-optic bundle described by Ferguson et al., 1996, *Nature Biotech.* 14:1681-1684, may be used to monitor mRNA abundance levels at a large number of sites simultaneously.

Signals are recorded and, in a preferred embodiment, analyzed by computer, e.g., using a 12 bit analog to digital board. In one embodiment the scanned image is despeckled using a graphics program (e.g., Hijaak Graphics Suite) and then analyzed using an image gridding program that creates a spreadsheet of the average hybridization at each wavelength at each site.

If necessary, an experimentally determined correction for "cross talk" (or overlap) between the channels for the two fluors may be made. For any particular hybridization site on the transcript array, a ratio of the emission of the two fluorophores is preferably calculated. The ratio is independent of the absolute expression level of the cognate gene, but is useful for genes whose expression is significantly modulated by drug administration, gene deletion, or any other tested event.

Preferably, in addition to identifying a perturbation as positive or negative, it is advantageous to determine the magnitude of the perturbation. This can be carried out by methods that will be readily apparent to those of skill in the art.

Other Methods of Transcriptional State Measurement

The transcriptional state of a cell may be measured by other gene expression technologies known in the art.

TAQMAN™ Based mRNA Levels Analysis

The RT-PCR (real-time quantitative PCR) assay utilizes an RNA reverse transcriptase to catalyze the synthesis of a DNA strand from an RNA strand, including an mRNA strand. The resultant DNA may be specifically detected and quantified and this process may be used to determine the levels of specific species of mRNA. One method for doing this is known under the Trademark TAQMAN (PE Applied Biosystems, Foster City, Calif.) and exploits the 5' nuclease activity of AMPLI TAQ GOLD™ DNA Polymerase to cleave a specific form of probe during a PCR reaction. This is referred to as a TAQMAN™ probe. See, Luthra R. et al., Novel 5' exonuclease-based real-time PCR assay for the detection of t(14; 18)(q32; q21) in patients with follicular lymphoma., *Am J. Pathol.*, Vol 153, (1998), pp.: 63-68. The probe consists of an oligonucleotide (usually ≈20 mer) with a 5'-reporter dye and a 3'-quencher dye. The fluorescent reporter dye, such as FAM (6-carboxyfluorescein), is covalently linked to the 5' end of the oligonucleotide. The reporter is quenched by TAMRA (6-carboxy-N,N,N',N'-tetramethylrhodamine) attached via a linker arm that is located at the 3' end. See, Kuimelis R G, et al., Structural analogues of TaqMan probes for real-time quantitative PCR., *Nucleic Acids Symp Ser.*, Vol 37, (1997), pp.: 255-256 and Mullah B. et al., Efficient synthesis of double dye-labeled oligodeoxyribonucleotide probes and their application in a real time PCR assay., *Nucleic Acids Res.*, Vol 15, (1998), pp.: 1026-1031. During the reaction, cleavage of the probe separates the reporter dye and the quencher dye, resulting in increased fluorescence of the reporter.

The accumulation of PCR products is detected directly by monitoring the increase in fluorescence of the reporter dye. See Heid C A, et al., Real time quantitative PCR., *Genome Res.*, Vol 6, (1996), pp.: 986-994. Reactions are characterised by the point in time during cycling when amplification of a PCR product is first detected rather than the amount of PCR product accumulated after a fixed number of cycles. The higher the starting copy number of nucleic acid target, the sooner a significant increase in fluorescence is observed. See, Gibson U E, et al., A novel method for real time quantitative RT-PCR, *Genome Res.*, Vol 6, (1996), pp.: 995-1001.

When the probe is intact, the proximity of the reporter dye to the quencher dye results in suppression of the reporter fluorescence primarily by Förster-type energy transfer. See, Lakowicz J R, et al., Oxygen quenching and fluorescence depolarization of tyrosine residues in proteins, *J Biol. Chem.*, Vol 258, (1983), pp.: 4794-4801. During PCR, if the target of interest is present, the probe specifically anneals between the forward and reverse primer sites. The 5'-3' nucleolytic activity of the AMPLITAQ GOLD™ DNA Polymerase cleaves the probe between the reporter and the quencher only if the probe hybridizes to the target. The probe fragments are then displaced from the target, and polymerization of the strand continues. This process occurs in every cycle and does not interfere with the exponential accumulation of product. The 3' end of the probe is blocked to prevent extension of the probe during PCR.

The passive reference is a dye included in the TAQMAN™ Buffer and does not participate in the 5' nuclease assay. The passive reference provides an internal reference to which the reporter dye signal can be normalized during data analysis. Normalization is necessary to correct for fluorescent fluctuations due to changes in concentration or volume.

Normalization is accomplished by dividing the emission intensity of the reporter dye by the emission intensity of the passive reference to obtain a ratio defined as the $R_n$ (normalized reporter) for a given reaction tube.

The threshold cycle or $C_t$ value is the cycle at which a statistically significant increase in $\Delta R_n$ is first detected. On a graph of $R_n$ versus cycle number, the threshold cycle occurs when the sequence detection application begins to detect the increase in signal associated with an exponential growth of PCR product.

To perform quantitative measurements serial dilutions of a cRNA (standard) are included in each experiment in order to construct a standard curve necessary for the accurate and fast mRNA quantitation. In order to estimate the reproducibility of the technique the amplification of the same cRNA simple may be performed multiple times.

Other technologies for measuring the transcriptional state of a cell produce pools of restriction fragments of limited complexity for electrophoretic analysis, such as methods combining double restriction enzyme digestion with phasing primers (see, e.g., European Patent 0 534858 A1, filed Sep. 24, 1992, by Zabeau et al.), or methods selecting restriction fragments with sites closest to a defined mRNA end (see, e.g., Prashar et al., 1996, *Proc. Natl. Acad. Sci. USA* 93:659-663).

Other methods statistically sample cDNA pools, such as by sequencing sufficient bases (e.g., 20-50 bases) in each of multiple cDNAs to identify each cDNA, or by sequencing short tags (e.g., 9-10 bases) which are generated at known positions relative to a defined mRNA end (see, e.g., Velculescu, 1995, *Science* 270:484-487). pathway pattern.

Measurement of Other Aspects

In various embodiments of the present invention, aspects of the biological state other than the transcriptional state, such as the translational state, the activity state, or mixed aspects can be measured in order to obtain drug and pathway responses. Details of these embodiments are described in this section.

Translational State Measurements

Expression of the protein encoded by the gene(s) can be detected by a probe which is detectably labeled, or which can be subsequently labeled. Generally, the probe is an antibody that recognizes the expressed protein.

As used herein, the term antibody includes, but is not limited to, polyclonal antibodies, monoclonal antibodies, humanized or chimeric antibodies, and biologically functional antibody fragments sufficient for binding of the antibody fragment to the protein.

For the production of antibodies to a protein encoded by one of the disclosed genes, various host animals may be immunized by injection with the polypeptide, or a portion thereof. Such host animals may include, but are not limited to, rabbits, mice, and rats, to name but a few. Various adjuvants may be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Camette-Guerin) and *Corynebacterium parvum*.

Polyclonal antibodies are heterogeneous populations of antibody molecules derived from the sera of animals immunized with an antigen, such as target gene product, or an antigenic functional derivative thereof. For the production of polyclonal antibodies, host animals, such as those described above, may be immunized by injection with the encoded protein, or a portion thereof, supplemented with adjuvants as also described above.

Monoclonal antibodies (mAbs), which are homogeneous populations of antibodies to a particular antigen, may be obtained by any technique that provides for the production of antibody molecules by continuous cell lines in culture. These include, but are not limited to, the hybridoma technique of Kohler and Milstein, *Nature,* 256:495-497 (1975); and U.S. Pat. No. 4,376,110. The human B-cell hybridoma technique of Kosbor et al., *Immunology Today,* 4:72 (1983); Cole et al., *Proc. Natl. Acad. Sci. USA,* 80:2026-2030 (1983); and the EBV-hybridoma technique, Cole et al., *Monoclonal Antibodies and Cancer Therapy*, Alan R. Liss, Inc., pp. 77-96 (1985). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies", Morrison et al., *Proc. Natl. Acad. Sci. USA,* 81:6851-6855 (1984); Neuberger et al., *Nature,* 312: 604-608 (1984); Takeda et al., *Nature,* 314:452-454 (1985), by splicing the genes from a mouse antibody molecule of appropriate antigen specificity together with genes from a human antibody molecule of appropriate biological activity can be used. A chimeric antibody is a molecule in which different portions are derived from different animal species, such as those having a variable or hypervariable region derived form a murine mAb and a human immunoglobulin constant region.

Alternatively, techniques described for the production of single chain antibodies, U.S. Pat. No. 4,946,778; Bird, *Science,* 242:423-426 (1988); Huston et al., *Proc. Natl. Acad. Sci. USA,* 85:5879-5883 (1988); and Ward et al., *Nature,* 334:544-546 (1989), can be adapted to produce differentially expressed gene-single chain antibodies. Single chain antibodies are formed by linking the heavy and light chain fragments of the Fv region via an amino acid bridge, resulting in a single chain polypeptide.

More preferably, techniques useful for the production of "humanized antibodies" can be adapted to produce antibodies to the proteins, fragments or derivatives thereof. Such techniques are disclosed in U.S. Pat. Nos. 5,932,448; 5,693,762; 5,693,761; 5,585,089; 5,530,101; 5,569,825; 5,625,126; 5,633,425; 5,789,650; 5,661,016; and 5,770,429.

Antibody fragments, which recognize specific epitopes, may be generated by known techniques. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed, Huse et al., *Science,* 246:1275-1281 (1989), to allow rapid and easy identification of monoclonal Fab fragments with the desired specificity.

The extent to which the known proteins are expressed in the sample is then determined by immunoassay methods that utilize the antibodies described above. Such immunoassay methods include, but are not limited to, dot blotting, western blotting, competitive and noncompetitive protein binding assays, enzyme-linked immunosorbant assays (ELISA), immunohistochemistry, fluorescence activated cell sorting (FACS), and others commonly used and widely described in scientific and patent literature, and many employed commercially.

Particularly preferred, for ease of detection, is the sandwich ELISA, of which a number of variations exist, all of which are intended to be encompassed by the present invention. For example, in a typical forward assay, unlabeled antibody is immobilized on a solid substrate and the sample to be tested brought into contact with the bound molecule after a suitable period of incubation, for a period of time sufficient to allow formation of an antibody-antigen binary complex. At this point, a second antibody, labeled with a reporter molecule capable of inducing a detectable signal, is then added and incubated, allowing time sufficient for the formation of a ternary complex of antibody-antigen-labeled antibody. Any unreacted material is washed away, and the presence of the antigen is determined by observation of a signal, or may be quantitated by comparing with a control sample containing known amounts of antigen. Variations on the forward assay include the simultaneous assay, in which both sample and antibody are added simultaneously to the bound antibody, or a reverse assay in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique. For the immunoassays of the present invention, the only limiting factor is that the labeled antibody must be an antibody that is specific for the protein expressed by the gene of interest.

The most commonly used reporter molecules in this type of assay are either enzymes, fluorophore- or radionuclide-containing molecules. In the case of an enzyme immunoassay an enzyme is conjugated to the second antibody, usually by means of glutaraldehyde or periodate. As will be readily recognized, however, a wide variety of different ligation techniques exist, which are well known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. A solution containing the appropriate substrate is then added to the tertiary complex. The substrate reacts with the enzyme linked to the second antibody, giving a qualitative visual signal, which may be further quantitated, usually spectrophotometrically, to give an evaluation of the amount of protein which is present in the serum sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

Measurement of the translational state may also be performed according to several additional methods. For example, whole genome monitoring of protein (i.e., the "proteome," Goffeau et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to testing or confirming a biological network model of interest. Methods for making monoclonal antibodies are well known (see, e.g., Harlow and Lane, 1988, Antibodies: A Laboratory Manual, Cold Spring Harbor, N.Y., which is incorporated in its entirety for all purposes). In a one preferred embodiment, monoclonal antibodies are raised against synthetic peptide fragments designed based on genomic sequence of the cell. With such an antibody array, proteins from the cell are contacted to the array and their binding is assayed with assays known in the art.

Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. See, e.g., Hames et al., 1990, Gel Electrophoresis of Proteins: A Practical Approach, IRL Press, New York; Shevchenko et al., 1996, *Proc. Nat'l Acad. Sci. USA* 93:1440-1445; Sagliocco et al., 1996, Yeast 12:1519-1533; Lander, 1996, *Science* 274: 536-539. The resulting electropherograms can be analyzed by numerous techniques, including mass spectrometric techniques, western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

Embodiments Based on Other Aspects of the Biological State

Although monitoring cellular constituents other than mRNA abundances currently presents certain technical difficulties not encountered in monitoring mRNAs, it will be apparent to those of skill in the art that the use of methods of this invention that the activities of proteins relevant to the characterization of cell function can be measured, embodiments of this invention can be based on such measurements. Activity measurements can be performed by any functional, biochemical, or physical means appropriate to the particular activity being characterized. Where the activity involves a chemical transformation, the cellular protein can be contacted with the natural substrates, and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In alternative and non-limiting embodiments, response data may be formed of mixed aspects of the biological state of a cell. Response data can be constructed from, e.g., changes in certain mRNA abundances, changes in certain protein abundances, and changes in certain protein activities.

The Detection of Nucleic Acids and Proteins as Markers

In a particular embodiment, the level of mRNA corresponding to the marker can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel, et al., Ed., *Current Protocols in Molecular Biology*, John Wiley & Sons, New York (1987-1999). Additionally, large numbers of tissue samples can readily be processed using techniques well-known to those of skill in the art, such as, for example, the single-step RNA isolation process of Chomczynski, U.S. Pat. No. 4,843,155 (1989).

The isolated mRNA can be used in hybridization or amplification assays that include, but are not limited to, Southern or Northern analyses, polymerase chain reaction analyses and probe arrays. One preferred diagnostic method for the detection of mRNA levels involve contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example, by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA corresponding to a marker of the present invention in a sample involves the process of nucleic acid amplification, e.g., by RT-PCR (the experimental embodiment set forth in Mullis, U.S. Pat. No. 4,683,202 (1987); ligase chain reaction, Barany, *Proc. Natl. Acad. Sci. USA,* 88:189-193 (1991); self-sustained sequence replication, Guatelli et al., *Proc. Natl. Acad. Sci. USA,* 87:1874-1878 (1990); transcriptional amplification system, Kwoh et al., *Proc. Natl. Ac. Sci. USA,* 86:1173-1177 (1989); Q-Beta Replicase, Lizardi et al., *Bio/Technology,* 6:1197 (1988); rolling circle replication, Lizardi et al., U.S. Pat. No. 5,854,033 (1988); or any other nucleic acid amplification method, followed by the detection of the amplified molecules using techniques well-known to those of skill in the art. These detection schemes are especially useful for the detection of the nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated form the cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, or between samples from different sources.

Alternatively, the expression level can be provided as a relative expression level. To determine a relative expression level of a marker, the level of expression of the marker is determined for 10 or more samples of normal versus disease biological samples, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

Preferably, the samples used in the baseline determination will be from patients who do not have the polymorphism. The choice of the cell source is dependent on the use of the relative expression level. Using expression found in normal tissues as a mean expression score aids in validating whether the marker assayed is specific (versus normal cells). In addition, as more data is accumulated, the mean expression value can be revised, providing improved relative expression values based on accumulated data.

Detection of Polypeptides

In another embodiment of the present invention, a polypeptide corresponding to a marker is detected. A preferred agent for detecting a polypeptide of the invention is an antibody capable of binding to a polypeptide corresponding to a marker of the invention, preferably an antibody with a detectable label. Antibodies can be polyclonal, or more preferably, monoclonal. An intact antibody, or a fragment thereof (e.g., Fab or F (ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end labeling of a DNA probe with biotin such that it can be detected with fluorescently labeled streptavidin.

Proteins from patients with psychotic disorders can be isolated using techniques that are well known to those of skill in the art. The protein isolation methods employed can, for example, be such as those described in Harlow and Lane, *Antibodies: A Laboratory Manual*, Harlow and Lane, Cold Spring Harbor Laboratory Press, Cold Spring Harbor, N.Y. (1988).

A variety of formats can be employed to determine whether a sample contains a protein that binds to a given antibody. Examples of such formats include, but are not limited to, enzyme immunoassay (EIA); radioimmunoasay (RIA), Western blot analysis and enzyme linked immunoabsorbant assay (ELISA). A skilled artisan can readily adapt known protein/antibody detection methods for use in determining whether cells express a marker of the present invention.

In one format, antibodies, or antibody fragments, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from patient cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

The invention also encompasses kits for detecting the presence of a polypeptide or nucleic acid corresponding to a marker of the invention in a biological sample (e.g., any body fluid including but not limited to, serum, plasma, lymph, cystic fluid, urine, stool, csf, acitic fluid, or blood and including biopsy samples of body tissue). For example, the kit can comprise a labeled compound or agent capable of detecting a polypeptide or an mRNA encoding a polypeptide corresponding to a marker of the invention in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for interpreting the results obtained using the kit.

For antibody-based kits, the kit can comprise, for example: 1) a first antibody (e.g., attached to a solid support) which binds to a polypeptide corresponding to a marker or the invention; and, optionally, 2) a second, different antibody which binds to either the polypeptide or the first antibody and is conjugated to a detectable label.

For oligonucleotide-based kits, the kit can comprise, for example: 1) an oligonucleotide, e.g., a detectably labeled oligonucleotide, which hybridizes to a nucleic acid sequence encoding a polypeptide corresponding to a marker of the invention; or 2) a pair of primers useful for amplifying a nucleic acid molecule corresponding to a marker of the invention. The kit can also comprise, e.g., a buffering agent, a preservative, or a protein-stabilizing agent. The kit can further comprise components necessary for detecting the detectable label (e.g., an enzyme or a substrate). The kit can also contain a control sample or a series of control samples, which can be assayed and compared to the test sample. Each component of the kit can be enclosed within an individual container and all of the various containers can be within a single package, along with instructions for interpreting the results of the assays performed using the kit.

Introduction of Antibodies into Cells

Characterization of intracellular proteins can be done in a variety of ways. For example, antibodies can be introduced into cells in many ways, including, for example, microinjection of antibodies into a cell (Morgan et al., 1988, *Immunology Today* 9:84-86) or transforming hybridoma mRNA encoding a desired antibody into a cell (Burke et al., 1984, *Cell* 36:847-858). In a further technique, recombinant antibodies can be engineering and ectopically expressed in a wide variety of non-lymphoid cell types to bind to target proteins as well as to block target protein activities (Biocca et al., 1995, *Trends in Cell Biology* 5:248-252). Expression of the antibody is preferably under control of a controllable promoter, such as the Tet promoter, or a constitutively active promoter (for production of saturating perturbations). A first step is the selection of a particular monoclonal antibody with appropriate specificity to the target protein (see below). Then sequences encoding the variable regions of the selected antibody can be cloned into various engineered antibody formats, including, for example, whole antibody, Fab fragments, Fv fragments, single chain Fv fragments (VH and VL regions united by a peptide linker) ("ScFv" fragments), diabodies (two associated ScFv fragments with different specificity), and so forth (Hayden et al., 1997, *Current Opinion in Immunology* 9:210-212). Intracellularly expressed antibodies of the various formats can be targeted into cellular compartments (e.g., the cytoplasm, the nucleus, the mitochondria, etc.) by expressing them as fusion's with the various known intracellular leader sequences (Bradbury et al., 1995, *Antibody Engineering* (vol. 2) (Borrebaeck ed.), pp. 295-361, IRL Press). In particular, the ScFv format appears to be particularly suitable for cytoplasmic targeting.

The Variety of Useful Antibody Types

Antibody types include, but are not limited to, polyclonal, monoclonal, chimeric, single chain, Fab fragments, and an Fab expression library. Various procedures known in the art may be used for the production of polyclonal antibodies to a target protein. For production of the antibody, various host animals can be immunized by injection with the target protein, such host animals include, but are not limited to, rabbit, mice, rats, etc. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as *bacillus* Calmette-Guerin (BCG) and *Corynebacterium parvum*.

Monoclonal Antibodies

For preparation of monoclonal antibodies directed towards a target protein, any technique that provides for the production of antibody molecules by continuous cell lines in culture may be used. Such techniques include, but are not restricted to, the hybridoma technique originally developed by Kohler and Milstein (1975, *Nature* 256: 495-497), the trioma technique, the human B-cell hybridoma technique (Kozbor et al., 1983, *Immunology Today* 4: 72), and the EBV hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. USA 80: 2026-2030), or by transforming human B cells with EBV virus in vitro (Cole et al., 1985, in Monoclonal Antibodies and Cancer Therapy, Alan R. Liss, Inc., pp. 77-96). In fact, according to the invention, techniques developed for the production of "chimeric antibodies" (Morrison et al., 1984, Proc. Natl. Acad. Sci. USA-81: 6851-6855; Neuberger et al., 1984, Nature 312:604-608; Takeda et al., 1985, Nature 314: 452-454) by splicing the genes from a mouse antibody molecule specific for the target protein together with genes from a human antibody molecule of appropriate biological activity can be used; such antibodies are within the scope of this invention.

Additionally, where monoclonal antibodies are advantageous, they can be alternatively selected from large antibody libraries using the techniques of phage display (Marks et al., 1992, J. Biol. Chem. 267:16007-16010). Using this technique, libraries of up to $10^{12}$ different antibodies have been expressed on the surface of fd filamentous phage, creating a "single pot" in vitro immune system of antibodies available for the selection of monoclonal antibodies (Griffiths et al., 1994, EMBO J. 13:3245-3260). Selection of antibodies from such libraries can be done by techniques known in the art, including contacting the phage to immobilized target protein, selecting and cloning phage bound to the target, and subcloning the sequences encoding the antibody variable regions into an appropriate vector expressing a desired antibody format.

According to the invention, techniques described for the production of single chain antibodies (U.S. Pat. No. 4,946,778) can be adapted to produce single chain antibodies specific to the target protein. An additional embodiment of the invention utilizes the techniques described for the construction of Fab expression libraries (Huse et al., 1989, Science 246: 1275-1281) to allow rapid and easy identification of monoclonal Fab fragments with the desired specificity for the target protein.

Antibody fragments that contain the idiotypes of the target protein can be generated by techniques known in the art. For example, such fragments include, but are not limited to: the $F(ab')_2$ fragment which can be produced by pepsin digestion of the antibody molecule; the Fab' fragments that can be generated by reducing the disulfide bridges of the $F(ab')_2$ fragment, the Fab fragments that can be generated by treating the antibody molecule with papain and a reducing agent, and Fv fragments.

In the production of antibodies, screening for the desired antibody can be accomplished by techniques known in the art, e.g., ELISA (enzyme-linked immunosorbent assay). To select antibodies specific to a target protein, one may assay generated hybridomas or a phage display antibody library for an antibody that binds to the target protein.

EXAMPLES

Example 1

Some aspects of the present invention can be demonstrated by an example showing the manner in which the correlation between the polymorphism in the CNTF gene and response to antipsychotic medication was first found.

In an effort to identify genetic factors that may associate with treatment response to Iloperidone, the relationship between a polymorphism in the CNTF (ciliary neurotrophic factor) gene (located on 11q12.2, the polymorphism being 103 G>A in GenBank sequence X55890 (Version 1), see PubMed: 9285965) and the clinical response to the antipsychotic Iloperidone in a clinical trial was investigated. This trial was a randomized, double-blind, placebo- and risperidone-controlled, multicenter study to evaluate the efficacy and safety of two non-overlapping dose ranges of Iloperidone (12 or 16 mg/d and 20 or 24 mg/d and risperidone (6 or 8 mg/d) compared with placebo, given twice-daily (b.i.d) for 42 days to schizophrenic patients followed by a long-term treatment phase with Iloperidone given once daily (q.d) at doses of 4, 8, 12, 16, or 24 mg/d for 46 weeks to patients with schizophrenia.

Pharmacogenetic analysis for candidate gene polymorphisms was conducted in Phase II of the clinical trial. It was determined whether the CNTF (ciliary neurotrophic factor) 103 G>A polymorphism (GenBank sequence X55890 (Version 1)) 103 G>A, (expressed protein alteration FS63 TER) was associated with any of the clinical parameters of efficacy studied in the course of the clinical trial and specifically changes in the BPRSA, Total PANNS, Positive PANNS, Negative PANNS and General PANNS scales.

A significant association was observed between the polymorphism in the CNTF gene and treatment response (BPRSA and Total PANNS scales) in the Iloperidone 12-16 mg treatment group. For description of the PANNS scale see, Kay S R et al. 1987, Schizophrenia Bulletin 13; 2:261-276. Individuals in this group that are of the GG type of the CNTF gene responded significantly better than the non-GG type and the response of the GG type versus the placebo is highly significant ($p<0.001$). These results show that antipsychotic medications, such as Ioperidone, have greater efficacy for the treatment of psychotic disorders, such as Schizophrenia, among individuals of the GG type of the CNTF gene. In this way a significant association between the CNTF 103 G>A polymorphism (GenBank sequence X55890 (Version 1)) and both the BPRSA and Total PANNS scales was identified.

A total of 207 unique blood samples were collected from the patients at the trial sites. The DNA was extracted by Covance (Geneva) using the PUREGENE™ DNA Isolation Kit (D-50K). The CNTF 103 G>A polymorphism (GenBank sequence X55890 (Version 1)) polymorphism was described by Takahashi, see, Takahashi et al. Nature Genet. 7: 79-84, 1994.

The probe sets for genotyping were designed and synthesized by Third Wave Technologies, Inc (Madison, Wis.). Genotyping was performed on 60 ng of genomic DNA using the INVADER® assay according to the manufacturer's recommendations (Third Wave Technologies, Inc, Madison Wis.), See Ryan D et al. Molecular Diagnosis Vol. 4 No 2 1999:135-144 and Lyamichev V et al. Nature Biotechnology Vol 17 1999:292-296, see also U.S. Pat. Nos. 5,846,717 and 6,001,567 (the disclosures of which are incorporated herein by reference in their entirety).

The analysis involved an analysis of variance test within treatments to check if any of the polymorphisms that were genotyped were significantly associated with the clinical parameters. The model consists of the percent change in the clinical parameters categorized by the genotypes. The association between genotype and the clinical parameters, when treatments are compared with placebo, is established using analysis of variance and analysis of covariance.

The terms in the analysis of variance model include percent change in the clinical parameters categorized by treatment for individuals with the same genotype. The terms in the analysis of covariance model include baseline values and endpoint values of the clinical parameters under study categorized by treatment groups for individuals with the same genotype. Analysis of variance within treatments revealed that the Total PANSS and BPRSA were significantly associated (p<0.001) with the CNTF 103 G>A polymorphism on CNTF for individuals treated with 12-16 mg dose of Iloperidone (Group A). The polymorphism is present on an intron and results in the modification of a splice site, which in turn results in a truncated mRNA. The result of these modifications is a varying clinical response.

Example 2

A 30 year old woman with new onset of a psychotic disorder is seen by a physician. After diagnosing a psychotic disorder that could be benefited by antipsychotic agents, her physician counsels the patient about the possibility of testing her for the presence of the polymorphism in the CNTF gene and explains what this result would mean with regard to the use of medication, including Iloperidone.

With the patients consent, the physician performs a test to determine the patient's genotype and determines that the patient has the GG form or the AA form of the CNTF gene at position 103. The physician discusses with the patient the short- and long-term consequences of antipsychotic medication treatment. The physician also discusses the other available treatment modalities and medications.

On the basis of these results, the physician recommends and the patient agrees to a trial of a medication such as Iloperidone to help control the symptoms of the psychotic disorder with the expectation that the patient will show a favorable response to relatively low doses with minimum side effects.

Example 3

A 52 year old man, with a psychotic disorder is seen by his physician with complaints of typical antipsychotic side effects such as akathesia and dyskinesias. The patient is being treated with Iloperidone and his psychotic symptoms are in good control but he is experiencing numerous side effects from the medication. The physician recommends genotyping and counsels the patient regarding the treatment options that the genotyping results would allow. The patient is tested and determined to have one of the genotypes, i.e. GG or AA, associated with the most favorable response to Iloperidone. On the basis of this result and the expected high sensitivity to Iloperidone the physician is able to recommend a treatment regimen with a substantially lower dose of Iloperidone with reduced likelihood of side effects. The physician is able to reduce the patients Iloperidone dose and reduce side effects and improve patient compliance without risking the worsening of the patients psychotic disorder with possible danger to the patient and others.

GLOSSARY AND DEFINITIONS

The following glossary and definitions are provided to facilitate understanding of certain terms used frequently in this specification.

As used herein the term "psychotic disorder" shall mean any pathologic psychological condition in which psychotic symptoms can or do occur and includes, but is not limited to the following; (also see, Diagnostic and Statistical Manual of Mental Disorders 4$^{th}$ Edition (DSM-IV) Francis A editor, American Psychiatric Press, Wash, D.C., 1994)
Schizophrenic Disorders
Schizophrenia, Catatonic, Subchronic, (295.21),
Schizophrenia, Catatonic, Chronic (295.22),
Schizophrenia, Catatonic, Subchronic with Acute Exacerbation (295.23),
Schizophrenia, Catatonic, Chronic with Acute Exacerbation (295.24),
Schizophrenia, Catatonic, in Remission (295.55),
Schizophrenia, Catatonic, Unspecified (295.20),
Schizophrenia, Disorganized, Subchronic (295.11),
Schizophrenia, Disorganized, Chronic (295.12),
Schizophrenia, Disorganized, Subchronic with Acute Exacerbation (295.13),
Schizophrenia, Disorganized, Chronic with Acute Exacerbation (295.14),
Schizophrenia, Disorganized, in Remission (295.15),
Schizophrenia, Disorganized, Unspecified (295.10),
Schizophrenia, Paranoid, Subchronic (295.31),
Schizophrenia, Paranoid, Chronic (295.32),
Schizophrenia, Paranoid, Subchronic with Acute Exacerbation (295.33),
Schizophrenia, Paranoid, Chronic with Acute Exacerbation (295.34),
Schizophrenia, Paranoid, in Remission (295.35),
Schizophrenia, Paranoid, Unspecified (295.30),
Schizophrenia, Undifferentiated, Subchronic (295.91),
Schizophrenia, Undifferentiated, Chronic (295.92),
Schizophrenia, Undifferentiated, Subchronic with Acute Exacerbation (295.93),
Schizophrenia, Undifferentiated, Chronic with Acute Exacerbation (295.94),
Schizophrenia, Undifferentiated, in Remission (295.95),
Schizophrenia, Undifferentiated, Unspecified (295.90),
Schizophrenia, Residual, Subchronic (295.61),
Schizophrenia, Residual, Chronic (295.62),
Schizophrenia, Residual, Subchronic with Acute Exacerbation (295.63),
Schizophrenia, Residual, Chronic with Acute Exacerbation (295.94),
Schizophrenia, Residual, in Remission (295.65),
Schizophrenia, Residual, Unspecified (295.60),
Delusional (Paranoid) Disorder (297.10),
Brief Reactive Psychosis (298.80),
Schizophreniform Disorder (295.40),
Schizoaffective Disorder (295.70),
Induced Psychotic Disorder (297.30),
Psychotic Disorder NOS (Atypical Psychosis) (298.90)
Affective Disorders
Major Depressive Disorder, Severe with Psychotic Features (296.33)
Bipolar I Disorder, Single Manic Episode, Severe with Psychotic Features (296.23)
Bipolar I Disorder, Most Recent Episode Hypomanic (296.43)
Bipolar I Disorder, Most Recent Episode Manic, Severe with Psychotic Features (296.43)
Bipolar I Disorder, Most Recent Episode Mixed, Severe with Psychotic Features (296.63)
Bipolar I Disorder Most Recent Episode Depressed, Severe with Psychotic Features (296.53)
Bipolar I Disorder, Most Recent Episode Unspecified (296.89)
Bipolar II Disorder (296.89)
Cyclothymic Disorder (301.13)
Bipolar Disorder NOS (366)
Mood Disorder Due To (General Medical Condition) (293.83)
Mood Disorder NOS (296.90)

Conduct Disorder, Solitary Aggressive Type (312.00),
Conduct Disorder, Undifferentiated Type (312.90),
Tourette's Disorder (307.23),
Chronic Motor Or Vocal Tic Disorder (307.22),
Transient Tic Disorder (307.21),
Tic Disorder NOS (307.20),
Psychoactive Substance Use Disorders
Alcohol Withdrawal Delirium (291.00),
Alcohol Hallucinosis (291.30),
Alcohol Dementia Associated with Alcoholism (291.20),
Amphetamine or Similarly Acting Sympathomimetic Intoxication (305.70),
Amphetamine or Similarly Acting Sympathomimetic Delirium (292.81),
Amphetamine or Similarly Acting Sympathomimetic Delusional Disorder (292.11),
Cannabis Delusional Disorder (292.11),
Cocaine Intoxication (305.60),
Cocaine Delirium (292.81),
Cocaine Delusional Disorder (292.11),
Hallucinogen Hallucinosis (305.30),
Hallucinogen Delusional Disorder (292.11),
Hallucinogen Mood Disorder (292.84),
Hallucinogen Post hallucinogen Perception Disorder (292.89),
Phencyclidine (PCP) or Similarly Acting Arylcyclohexylamine Intoxication (305.90),
Phencyclidine (PCP) or Similarly Acting Arylcyclohexylamine Delirium (292.81),
Phencyclidine (PCP) or Similarly Acting Arylcyclohexylamine Delusional Disorder (292. 11),
Phencyclidine (PCP) or Similarly Acting Arylcyclohexylamine Mood Disorder (292.84),
Phencyclidine (PCP) or Similarly Acting Arylcyclohexylamine Organic Mental Disorder NOS (292.90),
Other or Unspecified Psychoactive Substance Intoxication (305.90),
Other or Unspecified Psychoactive Substance Delirium (292.81),
Other or Unspecified Psychoactive Substance Dementia (292.82),
Other or Unspecified Psychoactive Substance Delusional Disorder (292.11),
Other or Unspecified Psychoactive Substance Hallucinosis (292.12),
Other or Unspecified Psychoactive Substance Mood Disorder (292.84),
Other or Unspecified Psychoactive Substance Anxiety Disorder (292.89),
Other or Unspecified Psychoactive Substance Personality Disorder (292.89),
Other or Unspecified Psychoactive Substance Organic Mental Disorder NOS (292.90)
Delirium (293.00),
Dementia (294.10),
Obsessive Compulsive Disorder (300.30),
Intermittent Explosive Disorder (312.34),
Impulse Control Disorder NOS (312.39)
Personality Disorders
Personality Disorder, Paranoid (301.00),
Personality Disorder, Schizoid (301.20),
Personality Disorder, Schizotypal (301.22),
Personality Disorder, Antisocial (301.70),
Personality Disorder, Borderline (301.83)

The term "antipsychotic agent" as used herein means any medication used to decrease or ameliorate the symptoms of psychosis in a person with a psychotic disorder and includes, but is not limited to the following compounds: Acetophenazine Maleate; Alentemol Hydrobromide; Alpertine; Azaperone; Batelapine Maleate; Benperidol; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Chlorpromazine; Chlorpromazine Hydrochloride; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; properidol; Etazolate Hydrochloride; Fenimide; Flucindole; Flumezapine; Fluphenazine Decanoate; Fluphenazine Enanthate; Fluphenazine Hydrochloride; Fluspiperone; Fluspirilene; Flutroline; Gevotroline Hydrochloride; Halopemide; Haloperidol; Haloperidol Decanoate; Iloperidone; Imidoline Hydrochloride; Lenperone; Mazapertine Succinate; Mesoridazine; Mesoridazine Besylate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palmitate; Piquindone Hydrochloride; Prochlorperazine Edisylate; Prochlorperazine Maleate; Promazine Hydrochloride; Quetiapine; Remoxipride; Remoxipride Hydrochloride; Risperidone; Rimcazole Hydrochloride; Seperidol Hydrochloride; Sertindole; Setoperone; Spiperone; Thioridazine; Thioridazine Hydrochloride; Thiothixene; Thiothixene Hydrochloride; Tioperidone Hydrochloride; Tiospirone Hydrochloride; Trifluoperazine Hydrochloride; Trifluperidol; Triflupromazine; Triflupromazine Hydrochloride; and Ziprasidone Hydrochloride.

In addition the term "antipsychotic agent" as used herein, includes so-called "atypical antipsychotic" medications including, but are not limited to:

Olanzapine, 2-methyl-4-(4-methyl-1-piperazinyl)-10H-thieno[2,3 b][1,5]benzodiazepine, is a known compound and is described in U.S. Pat. No. 5,229,382 as being useful for the treatment of schizophrenia, schizophreniform disorder, acute mania, mild anxiety states, and psychosis. U.S. Pat. No. 5,229,382 is herein incorporated by reference in its entirety;

Clozapine, 8-chloro-11-(4-methyl-1-piperazinyl)-5H-dibenzo[b,e][1,4]diazepine, is described in U.S. Pat. No. 3,539,573, which is herein incorporated by reference in its entirety. Clinical efficacy in the treatment of schizophrenia is described (Hanes, et al., Psychopharmacol. Bull., 24, 62 (1988));

Risperidone, 3-[2-[4-(6-fluoro-1,2-benzisoxazol-3-yl)piperidino]ethyl]-2-methyl-6,7,8,9-tetrahydro-4H-pyrido-[1, 2-a]pyrimidin-4-one, and its use in the treatment of psychotic diseases are described in U.S. Pat. No. 4,804,663, which is herein incorporated by reference in its entirety;

Sertindole, 1-[2-[4-[5-chloro-1-(4-fluorophenyl)-1H-indol-3-yl]-1-piperidinyl]ethyl]imidazolidin-2-one, is described in U.S. Pat. No. 4,710,500. Its use in the treatment of schizophrenia is described in U.S. Pat. Nos. 5,112,838 and 5,238,945. U.S. Pat. Nos. 4,710,500; 5,112,838; and 5,238, 945 are herein incorporated by reference in their entirety;

Quetiapine, 5-[2-(4-dibenzo[b,f][1,4]thiazepin-11-yl-1-piperazinyl)ethoxy-]ethanol, and its activity in assays which demonstrate utility in the treatment of schizophrenia are described in U.S. Pat. No. 4,879,288, which is herein incorporated by reference in its entirety. Quetiapine is typically administered as its (E)-2-butenedioate (2:1) salt; and;

Ziprasidone, 5-[2-[4-(1,2-benzoisothiazol-3-yl)-1-piperazinyl]ethyl]-6-chloro-1,3-dihydro-2H-indol-2-one, is typically administered as the hydrochloride monohydrate. The compound is described in U.S. Pat. Nos. 4,831,031 and 5,312,925. Its activity in assays which demonstrate utility in the treatment of schizophrenia are described in U.S. Pat. No. 4,831,031. U.S. Pat. Nos. 4,831,031 and 5,312,925 are herein incorporated by reference in their entirety. Similarly, when the invention is regarded in its broadest sense, the second component compound is a compound which functions as a serotonin reuptake inhibitor.

"Significant level" as used herein, in reference to the level of expression of mRNA or polypeptide product from a particular allele (for example the polymorphism in the CNTF gene (located on 11q12.2), the polymorphism being 103 G>A in GenBank sequence X55890, see PubMed: 9285965) means that level of expression that would lead one of skill in the art to believe that the allele in question was present.

"Antibodies" as used herein includes polyclonal and monoclonal antibodies, chimeric, single chain, and humanized antibodies, as well as Fab fragments, including the products of an Fab or other immunoglobulin expression library.

"Polynucleotide" generally refers to any polyribonucleotide (RNA) or polydeoxyribonucleotide (DNA), which may be unmodified or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons.

"Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any polypeptide comprising two or more amino acids joined to each other by peptide bonds or modified peptide bonds, —i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini.

It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racernization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W.H. Freeman and Company, New York, 1993; Wold, F., Post-translational Protein Modifications: Perspectives and Prospects, 1-12, in Post-translational Covalent Modification of Proteins, B. C. Johnson, Ed., Academic Press, New York, 1983; Seifter et al., "Analysis for protein modifications and nonprotein cofactors", Meth Enzymol, 182, 626-646, 1990, and Rattan et al., "Protein Synthesis: Post-translational Modifications and Aging", Ann NY Acad Sci, 663, 48-62, 1992).

"Fragment" of a polypeptide sequence refers to a polypeptide sequence that is shorter than the reference sequence but that retains essentially the same biological function or activity as the reference polypeptide.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from the reference polypeptide. Generally, alterations are limited so that the sequences of the reference polypeptide and the variant are closely similar overall and, in many regions, identical. A variant and reference polypeptide may differ in amino acid sequence by one or more substitutions, insertions, deletions in any combination. A substituted or inserted amino acid residue may or may not be one encoded by the genetic code. Typical conservative substitutions include Gly, Ala; Val, lie, Leu; Asp, Glu; Asn, Gln-I Ser. Thr; Lys, Arg; and Phe and Tyr. A variant of a polynucleotide or polypeptide may be naturally occurring such as an allele, or it may be a variant that is not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylation, ADP ribosylation and the like. Embodiments include methylation of the N-terminal amino acid, phosphorylations of serines and threonines and modification of C-terminal glycines.

"Polymorphism"—The sequence variation observed in an individual at a polymorphic site. Polymorphisms include nucleotide substitutions, insertions, deletions and microsatellites and may, but need not, result in detectable differences in gene expression or protein function.

"Polymorphic site (PS)"—A position within a locus at which at least two alternative sequences are found in a population, the most frequent of which has a frequency of no more than 99%.

"Polymorphic variant"—A gene, mRNA, cDNA, polypeptide or peptide whose nucleotide or amino acid sequence varies from a reference sequence due to the presence of a polymorphism in the gene.

"Polymorphism data"—Information concerning one or more of the following for a specific gene: location of polymorphic sites; sequence variation at those sites; frequency of polymorphisms in one or more populations; the different genotypes and/or haplotypes determined for the gene; frequency of one or more of these genotypes and/or haplotypes in one or more populations; any known association(s) between a trait and a genotype or a haplotype for the gene.

"Polymorphism database"—A collection of polymorphism data arranged in a systematic or methodical way and capable of being individually accessed by electronic or other means.

"Single Nucleotide Polymorphism" (SNP) refers to the occurrence of nucleotide variability at a single nucleotide position in the genome, within a population. An SNP may occur within a gene or within intergenic regions of the genome. SNPs can be assayed using Allele Specific Amplification (ASA). For the process at least 3 primers are required. A common primer is used in reverse complement to the polymorphism being assayed. This common primer can be between 50 and 1500 bps from the polymorphic base. The other two (or more) primers are identical to each other except that the final 3' base wobbles to match one of the two (or more) alleles that make up the polymorphism. Two (or more) PCR reactions are then conducted on sample DNA, each using the common primer and one of the Allele Specific Primers.

"Splice Variant" as used herein refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of which may encode different amino acid sequences. The term splice variant also refers to the proteins encoded by the above cDNA molecules.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared.

"Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Ortholog" refers to a polynucleotide or polypeptide that is the functional equivalent of the polynucleotide or polypeptide in another species. "Paralog" refers to a polynucleotide or polypeptide that within the same species which is functionally similar.

"Fusion protein" refers to a protein encoded by two, unrelated, fused genes or fragments thereof. Examples have been disclosed in U.S. Pat. Nos. 5,541,087 and 5,726,044 (both of which are hereby incorporated by reference for all purposes). In the case of Fc-PGPCR-3, employing an immunoglobulin Fc region as a part of a fusion protein is advantageous for performing the functional expression of Fc-PGPCR-3 or fragments of PGPCR-3, to improve pharmacokinetic properties of such a fusion protein when used for therapy and to generate a dimeric Fc-PGPCR-3. The Fc-PGPCR-3 DNA construct comprises in 5' to 3' direction, a secretion cassette, i.e. a signal sequence that triggers export from a mammalian cell, DNA encoding an immunoglobulin Fc region fragment, as a fusion partner, and a DNA encoding Fc-PGPCR-3 or fragments thereof. In some uses it would be desirable to be able to alter the intrinsic functional properties (complement binding, Fc-Receptor binding) by mutating the functional Fc sides while leaving the rest of the fusion protein untouched or delete the Fc part completely after expression.

"Allele"—A particular form of a genetic locus, distinguished from other forms by its particular nucleotide sequence.

"Candidate gene"—A gene which is hypothesized to be responsible for a disease, condition, or the response to a treatment, or to be correlated with one of these.

"Gene"—A segment of DNA that contains all the information for the regulated biosynthesis of an RNA product, including promoters, exons, introns, and other untranslated regions that control expression.

"Genotype"—An unphased 5' to 3' sequence of nucleotide pair(s) found at one or more polymorphic sites in a locus on a pair of homologous chromosomes in an individual. As used herein, genotype includes a full-genotype and/or a sub-genotype as described below.

"Full-genotype"—The unphased 5' to 3' sequence of nucleotide pairs found at all known polymorphic sites in a locus on a pair of homologous chromosomes in a single individual.

"Sub-genotype"—The unphased 5' to 3' sequence of nucleotides seen at a subset of the known polymorphic sites in a locus on a pair of homologous chromosomes in a single individual.

"Genotyping"—A process for determining a genotype of an individual.

"Haplotype"—A 5' to 3' sequence of nucleotides found at one or more polymorphic sites in a locus on a single chromosome from a single individual. As used herein, haplotype includes a full-haplotype and/or a sub-haplotype as described below.

"Full-haplotype"—The 5' to 3' sequence of nucleotides found at all known polymorphic sites in a locus on a single chromosome from a single individual.

"Sub-haplotype"—The 5' to 3' sequence of nucleotides seen at a subset of the known polymorphic sites in a locus on a single chromosome from a single individual.

"Haplotype pair"—The two haplotypes found for a locus in a single individual.

"Haplotyping"—A process for determining one or more haplotypes in an individual and includes use of family pedigrees, molecular techniques and/or statistical inference.

"Haplotype data"—Information concerning one or more of the following for a specific gene: a listing of the haplotype pairs in each individual in a population; a listing of the different haplotypes in a population; frequency of each haplotype in that or other populations, and any known associations between one or more haplotypes and a trait.

"Isoform"—A particular form of a gene, mRNA, cDNA or the protein encoded thereby, distinguished from other forms by its particular sequence and/or structure.

"Isogene"—One of the isoforms of a gene found in a population. An isogene contains all of the polymorphisms present in the particular isoform of the gene.

"Isolated"—As applied to a biological molecule such as RNA, DNA, oligonucleotide, or protein, isolated means the molecule is substantially free of other biological molecules such as nucleic acids, proteins, lipids, carbohydrates, or other material such as cellular debris and growth media. Generally, the term "isolated" is not intended to refer to a complete absence of such material or to absence of water, buffers, or salts, unless they are present in amounts that substantially interfere with the methods of the present invention.

"Linkage"—describes the tendency of genes to be inherited together as a result of their location on the same chromosome; measured by percent recombination between loci.

"Linkage disequilibrium"—describes a situation in which some combinations of genetic markers occur more or less frequently in the population than would be expected from their distance apart. It implies that a group of markers has been inherited coordinately. It can result from reduced recombination in the region or from a founder effect, in which there has been insufficient time to reach equilibrium since one of the markers was introduced into the population.

"Locus"—A location on a chromosome or DNA molecule corresponding to a gene or a physical or phenotypic feature.

"Naturally-occurring"—A term used to designate that the object it is applied to, e.g., naturally-occurring polynucleotide or polypeptide, can be isolated from a source in nature and which has not been intentionally modified by man.

"Nucleotide pair"—The nucleotides found at a polymorphic site on the two copies of a chromosome from an individual.

"Phased"—As applied to a sequence of nucleotide pairs for two or more polymorphic sites in a locus, phased means the combination of nucleotides present at those polymorphic sites on a single copy of the locus is known.

"Unphased"—As applied to a sequence of nucleotide pairs for two or more polymorphic sites in a locus, unphased means the combination of nucleotides present at those polymorphic sites on a single copy of the locus is not known.

"Population group"—A group of individuals sharing a common characteristic such as ethnogeographic origin, medical condition, response to treatment etc.

"Reference population"—A group of subjects or individuals who are predicted to be representative of 1 or more characteristics of the population group. Typically, the reference population represents the genetic variation in the population at a certainty level of at least 85%, preferably at least 90%, more preferably at least 95% and even more preferably at least 99%.

"Subject"—A human individual whose genotypes or haplotypes or response to treatment or disease state are to be determined.

"Treatment"—A stimulus administered internally or externally to a subject.

References Cited

All references cited herein are incorporated herein by reference in their entirety and for all purposes to the same extent as if each individual publication or patent or patent application was specifically and individually indicated to be incorporated by reference in its entirety for all purposes. The discussion of references herein is intended merely to summarise the assertions made by their authors and no admission is made that any reference constitutes prior art. Applicants reserve the right to challenge the accuracy and pertinence of the cited references.

In addition, all GenBank accession numbers, Unigene Cluster numbers and protein accession numbers cited herein are incorporated herein by reference in their entirety and for all purposes to the same extent as if each such number was specifically and individually indicated to be incorporated by reference in its entirety for all purposes.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatus within the scope of the invention, in addition to those enumerated herein, will be apparent to those skilled in the art from the foregoing description and accompanying drawings. Such modifications and variations are intended to fall within the scope of the appended claims. The present invention is to be limited only by the terms of the appended claims, along with the full scope of equivalents to which such claims are entitled.

What is claimed is:

1. A method of treating a psychotic disorder in a human individual in need of such treatment comprising:
   a) determining, in a biological sample, for each of the two copies of the CNTF gene present in the individual the identity of the nucleotide pair at the polymorphic site 103G>A in GenBank sequence reference No. X55890 (Version 1),
   b) detecting the presence of GG at position 103 of the human individual and
   c) treating the individual with GG at position 103 with iloperidone.

2. A method according to claim 1, wherein determining includes use of a kit for the identification of the individual's polymorphism pattern at the CNTF polymorphic site at 103 G>A, the kit comprising a means for determining a genetic polymorphism pattern at the CNTF polymorphic site at 103 G>A.

3. A method according to claim 1, wherein the method is performed ex vivo.

4. A method of treating a psychotic disorder in a human individual in need of such treatment comprising:
   a) determining, in a biological sample, the level of mRNA of the CNTF gene wherein the CNTF gene is GenBank sequence reference No. X55890 (Version 1),
   b) comparing the level mRNA determined in the biological sample, to a value of mRNA levels corresponding to a GG at position 103 of the CNTF gene
   c) determining the human individual is GG at position 103 and
   d) treating the individual with GG at position 103 with iloperidone.

5. A method according to claim 4, wherein detecting includes use of a kit for the identification of an mRNA expression product of the CNTF gene, the kit comprising a means for determining the mRNA expression product of the CNTF gene.

* * * * *